(12) United States Patent
Breitenstein et al.

(10) Patent No.: US 7,569,566 B2
(45) Date of Patent: Aug. 4, 2009

(54) INHIBITORS OF TYROSINE KINASES

(75) Inventors: Werner Breitenstein, Basel (CH); Pascal Furet, Thann (FR); Sandra Jacob, Rantzwiller (FR); Paul W Manley, Arlesheim (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/061,334

(22) Filed: Apr. 2, 2008

(65) Prior Publication Data
US 2008/0188451 A1 Aug. 7, 2008

Related U.S. Application Data

(63) Continuation of application No. 11/607,542, filed on Dec. 1, 2006, now abandoned, which is a continuation of application No. 10/520,359, filed as application No. PCT/EP03/07198 on Jul. 4, 2003, now Pat. No. 7,169,791.

(30) Foreign Application Priority Data

Jul. 5, 2002 (GB) ................................. 0215676.8
Dec. 20, 2002 (GB) ................................. 0229893.3

(51) Int. Cl.
C07D 401/14 (2006.01)
A61K 31/506 (2006.01)

(52) U.S. Cl. ............................. 514/235.8; 514/252.18; 514/275; 544/122; 544/295; 544/331

(58) Field of Classification Search ................ 544/331, 544/122, 295; 514/275, 235.8, 252.18
See application file for complete search history.

(56) References Cited

U.S. PATENT DOCUMENTS

| | | | |
|---|---|---|---|
| 5,516,775 A | 5/1996 | Zimmermann et al. | |
| 5,521,184 A | 5/1996 | Zimmermann | |
| 2006/0014742 A1 | 1/2006 | Asaki et al. | |

FOREIGN PATENT DOCUMENTS

| | | |
|---|---|---|
| EP | 0 588 762 | 3/1994 |
| JP | 6-184116 | 7/1994 |
| WO | 95/09853 | 4/1995 |
| WO | 02/46170 | 6/2002 |
| WO | 02/46171 | 6/2002 |
| WO | 2004/002963 | 1/2004 |

OTHER PUBLICATIONS

Zimmermann et al., "Potent and Selective Inhibitors of the ABL-Kinase: Phenylamino-Pyrimidine (PAP) Derivatives," Bioorganic & Medical Chemistry Letters, vol. 7, No. 2, pp. 187-192 (1997).
Zimmermann et al., "Phenylamino-Pyrimidine (PAP)—Derivatives: A New Class of Potent and Highly Selective PDGF-Receptor Autophosphorylatin Inhibitors," Bioorganic & Medicinal Chemistry Letters, vol. 6, No. 11, pp. 1221-1226 (1996).
Paul et al., "Preparation of Substituted N-Phenyl-4-aryl-2-pyrimidinamines as Mediator Release Inhibitors," J. Med. Chem., vol. 36, pp. 2716-2725 (1993).
Bhat et al., "Interactions of CBL with BCR-ABL and CRKL in BCR-ABL transformed Myeloid Cells," The Journal of Biological Chemistry, vol. 272, No. 26, Issue of Jun. 27, pp. 16170-16175 (1997).
Shibuya et al., "Nucleotide sequence and expression of a novel human receptor-type tyrosine kinase gene (flt) closely related to the fms family," Oncogene, vol. 5, pp. 519-524 (1990).
Dorsey et al., "Discovery of a Novel ABL Tyrosine Kinase Inhibitor That Selectively Induces Apoptosis of BCR-ABL-Positive Leukemic Cells," Abstracts/Hematology, vol. 28(7), Suppl. 1, p. 49 (2000).
Simone, Oncology: Introduction, Cecil Textbook of Medicine, 20th Edition, vol. 1, pp. 1004-1010 (1996).
Traxler, "Protein tyrosine kinase inhibitors in cancer treatment," Exp. Opin. Ther. Patents, 7(6):571-588 (1997).

*Primary Examiner*—Deepak Rao
(74) *Attorney, Agent, or Firm*—Lydia T. McNally

(57) ABSTRACT

The invention relates to compounds of formula

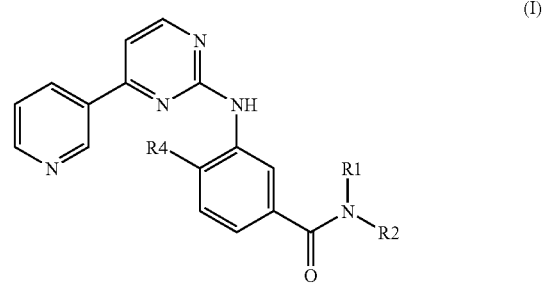

(I)

wherein the substituents R1, R2 and R4 have the meaning as set forth and explained in the description of the invention, to processes for the preparation of these compounds, pharmaceutical compositions containing same, the use thereof optionally in combination with one or more other pharmaceutically active compounds for the therapy of a disease which responds to an inhibition of protein kinase activity, especially a neoplastic disease, in particular leukaemia, and a method for the treatment of such a disease.

7 Claims, No Drawings

INHIBITORS OF TYROSINE KINASES

This application is a continuation of U.S. patent application Ser. No. 11/607,542, filed Dec. 1, 2006 now abandoned, which is a continuation of U.S. application Ser. No. 10/520,359, filed Sep. 12, 2005 now U.S. Pat. No. 7,169,791, which is a 371 of International Application No. PCT/EP03/07198, filed Jul. 4, 2003.

The invention relates to novel substituted pyrimidinylaminobenzamides, processes for the preparation thereof, pharmaceutical compositions containing same, the use thereof optionally in combination with one or more other pharmaceutically active compounds for the therapy of a disease which responds to an inhibition of protein kinase activity, especially a neoplastic disease, in particular leukaemia, and a method for the treatment of such a disease.

BACKGROUND OF THE INVENTION

Protein kinases (PKs) are enzymes which catalyze the phosphorylation of specific serine, threonine or tyrosine residues in cellular proteins. These post-translational modifications of substrate proteins act as molecular switches regulating cell proliferation, activation and/or differentiation. Aberrant or excessive PK activity has been observed in many disease states including benign and malignant proliferative disorders. In a number of cases, it has been possible to treat diseases, such as proliferative disorders, by making use of PK inhibitors in vitro and in vivo.

In view of the large number of protein kinase inhibitors and the multitude of proliferative and other PK-related diseases, there is an ever-existing need to provide novel classes of compounds that are useful as PK inhibitors and thus in the treatment of these PTK related diseases. What is required are new classes of pharmaceutically advantageous PK inhibiting compounds.

The Philadelphia Chromosome is a hallmark for chronic myelogenous leukaemia (CML) and carries a hybrid gene that contains N-terminal exons of the bcr gene and the major C-terminal part (exons 2-11) of the c-abl gene. The gene product is a 210 kD protein (p210 Bcr-Abl). The Abl-part of the Bcr-Abl protein contains the abl-tyrosine kinase which is tightly regulated in the wild type c-abl, but constitutively activated in the Bcr-Abl fusion protein. This deregulated tyrosine kinase interacts with multiple cellular signaling pathways leading to transformation and deregulated proliferation of the cells (Lugo et al., Science 247, 1079 [1990]).

GENERAL DESCRIPTION OF THE INVENTION

It has now been found that various compounds of the pyrimidinylaminobenzamide class show inhibition of protein kinase activity. The compounds of formula I, described below in more detail, especially show inhibition of one or more tyrosine kinases, such as c-Abl, Bcr-Abl, the receptor tyrosine kinases PDGF-R, Flt3, VEGF-R, EGF-R, and c-Kit, as well as combinations of two or more of these; in the case of novel pyrimidinylaminobenzamides according to the invention, the compounds are appropriate for the inhibition of these and/or other protein kinases, especially those mentioned above and/or for the inhibition of mutants of these enzymes, especially of Bcr-Abl, for example the Glu255->Valine mutant. In view of these activities, the compounds can be used for the treatment of diseases related to especially aberrant or excessive activity of such types of kinases, especially those mentioned.

DETAILED DESCRIPTION OF THE INVENTION

The invention relates to a compound of formula I,

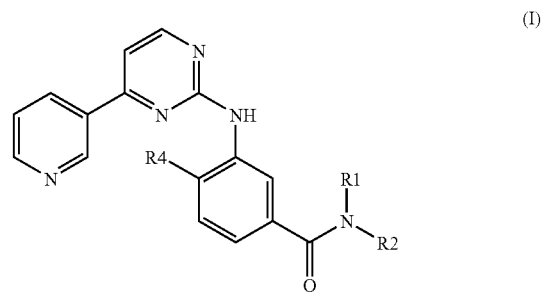

wherein $R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;

$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

and $R_3$ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

or wherein $R_1$ and $R_2$ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;

$R_4$ represents hydrogen, lower alkyl, or halogen;

and a N-oxide or a pharmaceutically acceptable salt of such a compound.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)- configuration. The compounds may thus be present as mixtures of isomers or as pure isomers, preferably as enantiomer-pure diastereomers.

The invention relates also to possible tautomers of the compounds of formula I.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or lower alkylcarbonyl, in particular acetyl.

An aryl group is an aromatic radical which is bound to the molecule via a bond located at an aromatic ring carbon atom of the radical. In a preferred embodiment, aryl is an aromatic radical having 6 to 14 carbon atoms, especially phenyl, naphthyl, tetrahydronaphthyl, fluorenyl or phenanthrenyl, and is unsubstituted or substituted by one or more, preferably up to three, especially one or two substituents, especially selected from amino, mono- or disubstituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora (—B(OH)$_2$), heterocyclyl, a mono- or bicyclic heteroaryl group and lower alkylene dioxy bound at adjacent C-atoms of the ring, such as methylene dioxy. Aryl is more preferably phenyl, naphthyl or tetrahydronaphthyl, which in each case is either unsubstituted or independently substituted by one or two substituents selected from the group comprising halogen, especially fluorine, chlorine, or bromine; hydroxy; hydroxy etherified by lower alkyl, e.g. by methyl, by halogen-lower alkyl, e.g. trifluoromethyl, or by phenyl; lower alkylene dioxy bound to two adjacent C-atoms, e.g. methylenedioxy, lower alkyl, e.g. methyl or propyl; halogen-lower alkyl, e.g. trifluoromethyl; hydroxy-lower alkyl, e.g. hydroxymethyl or 2-hydroxy-2-propyl; lower alkoxy-lower alkyl; e.g. methoxymethyl or 2-methoxyethyl; lower alkoxycarbonyl-lower alkyl, e.g. methoxy-carbonylmethyl; lower alkynyl, such as 1-propynyl; esterified carboxy, especially lower alkoxycarbonyl, e.g. methoxycarbonyl, n-propoxy carbonyl or iso-propoxy carbonyl; N-mono-substituted carbamoyl, in particular carbamoyl monosubstituted by lower alkyl, e.g. methyl, n-propyl or iso-propyl; amino; lower alkylamino, e.g. methylamino; di-lower alkylamino, e.g. dimethylamino or diethylamino; lower alkylene-amino, e.g. pyrrolidino or piperidino; lower oxaalkylene-amino, e.g. morpholino, lower azaalkylene-amino, e.g. piperazino, acylamino, e.g. acetylamino or benzoylamino; lower alkylsulfonyl, e.g. methylsulfonyl; sulfamoyl; or phenylsulfonyl.

A cycloalkyl group is preferably cyclopropyl, cyclopentyl, cyclohexyl or cycloheptyl, and may be unsubstituted or substituted by one or more, especially one or two, substitutents selected from the group defined above as substituents for aryl, most preferably by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Mono- or disubstituted amino is especially amino substituted by one or two radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino.

Disubstituted amino is also lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazino or N-methoxycarbonylpiperazino.

Halogen is especially fluorine, chlorine, bromine, or iodine, especially fluorine, chlorine, or bromine.

Etherified hydroxy is especially $C_8$-$C_{20}$alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic hetero-aryl comprising one or two nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bicyclic heteroaryl group comprising zero, one, two or three ring nitrogen atoms and zero or one oxygen atom and zero or one sulfur atom, which groups in each case are unsubstituted or mono- or polysubstituted, refers to a heterocyclic moiety that is unsaturated in the ring binding the heteroaryl radical to the rest of the molecule in formula I and is preferably a ring, where in the binding ring, but optionally also in any annealed ring, at least one carbon atom is replaced by a heteroatom selected from the group consisting of nitrogen, oxygen and sulfur; where the binding ring preferably has 5 to 12, more preferably 5 or 6 ring atoms; and which may be unsubstituted or substituted by one or more, especially one or two, substitutents selected from the group defined above as substitutents for aryl, most preferably by lower alkyl, such as methyl, lower alkoxy, such as methoxy or ethoxy, or hydroxy. Preferably the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxaloyl, quinazolinyl, quinolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, benzo[d]pyrazolyl, thienyl, and furanyl. In one preferred embodiment of the invention the pyridyl radical is substituted by hydroxy in ortho position to the nitrogen atom and hence exists at least partially in the form of the corresponding tautomer which is pyridin-(1H)2-one. In another preferred embodiment, the pyrimidinyl radical is substituted by hydroxy both in position 2 and 4 and hence exists in several tautomeric forms, e.g. as pyrimidine-(1H, 3H)2,4-dione.

Heterocyclyl is especially a five, six or seven-membered heterocyclic system with one or two heteroatoms selected from the group comprising nitrogen, oxygen, and sulfur, which may be unsaturated or wholly or partly saturated, and is unsubstituted or substituted especially by lower alkyl, such as methyl, phenyl-lower alkyl, such as benzyl, oxo, or heteroaryl, such as 2-piperazinyl; heterocyclyl is especially 2- or 3-pyrrolidinyl, 2-oxo-5-pyrrolidinyl, piperidinyl, N-benzyl-4-piperidinyl, N-lower alkyl-4-piperidinyl, N-lower alkyl-piperazinyl, morpholinyl, e.g. 2- or 3-morpholinyl, 2-oxo-1H-azepin-3-yl, 2-tetrahydrofuranyl, or 2-methyl-1,3-dioxolan-2-yl.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula I and N-oxides thereof have valuable pharmacological properties, as described hereinbefore and hereinafter.

The efficacy of the compounds of the invention as inhibitors of c-Abl, Bcr-Abl, and VEGF-receptor tyrosine kinase activity can be demonstrated as follows:

Test for activity against c-Abl protein tyrosine kinase. The test is conducted as a filter binding assay as follows: The His-tagged kinase domain of c-Abl is cloned and expressed in the baculovirus/Sf9 system as described by Bhat et al., J Biol. Chem. 272, 16170-5 (1997). A protein of 37 kD (c-Abl kinase) is purified by a two-step procedure over a Cobalt metal chelate column followed by an anion exchange column with a yield of 1-2 mg/L of Sf9 cells. The purity of the c-Abl kinase is >90% as judged by SDS-PAGE after Coomassie blue staining. The assay contains: c-Abl kinase (50 ng), 20 mM Tris.HCl, pH 7.5, 10 mM $MgC_2$, 10 µM $Na_3VO_4$, 1 mM DTT and 0.06 µCi/assay [$Y^{33}$ P]-ATP (5 µM ATP) using 30 µg/mL poly-Ala,Glu,Lys,Tyr-6:2:5:1 (Poly-AEKY, Sigma P1152) in the presence of 1% DMSO, total volume of 30 µL. Reactions are terminated by adding 10 µL of 250 mM EDTA, and 30 µL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 μL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 μL/well of Microscint™ (Packard).

Test for activity against Bcr-Abl. The murine myeloid progenitor cell line 32Dcl3 transfected with the p210 Bcr-Abl expression vector pGDp210Bcr/Abl (32D-bcr/abl) was obtained from J. Griffin (Dana Faber Cancer Institute, Boston, Mass., USA). The cells express the fusion Bcr-Abl protein with a constitutively active abl kinase and proliferate growth factor independent. The cells are expanded in RPMI 1640 (AMIMED), 10% fetal calf serum, 2 mM glutamine (Gibco) ("complete medium"), and a working stock is prepared by freezing aliquots of $2 \times 10^6$ cells per vial in freezing medium (95% FCS, 5% DMSO (SIGMA)). After thawing, the cells are used during maximally 10-12 passages for the experiments.

For cellular assays, compounds are dissolved in DMSO and diluted with complete medium to yield a starting concentration of 10 μM followed by preparation of serial 3-fold dilutions in complete medium. 200'000 32D-Bcr/Abl cells in 50 μL complete medium are seeded per well in 96 well round bottom tissue culture plates. 50 μL per well of serial 3-fold dilutions of the test compound are added to the cells in triplicates. Untreated cells are used as control. The compound is incubated together with the cells for 90 min at 37° C., 5% $CO_2$, followed by centrifugation of the tissue culture plates at 1300 rpm (Beckmann GPR centrifuge) and removal of the supernatants by careful aspiration taking care not to remove any of the pelleted cells. The cell pellets are lysed by addition of 150 μL lysis buffer (50 mM Tris/HCl, pH 7.4, 150 mM sodium chloride, 5 mM EDTA, 1 mM EGTA, 1% NP-40, 2 mM sodium ortho-vanadate, 1 mM PMSF, 50 μg/mL aprotinin and 80 μg/mL leupeptin) and either used immediately for the ELISA or stored frozen in the plates at −20° C. until usage. Black ELISA plates (Packard HTRF-96 black plates) are precoated over night at 4° C. with 50 ng/well of the rabbit polyclonal anti-abl-SH3 domain Ab 06-466 from Upstate in 50 μL PBS. After washing 3 times with 200 μL/well PBS containing 0.05% Tween20 (PBST) and 0.5% TopBlock (Juro), residual protein binding sites are blocked with 200 μL/well PBST, 3% TopBlock for 4 h at room temperature followed by incubation with 50 μL lysates of untreated or compound-treated cells (20 μg total protein per well) for 3-4 h at 4° C. After 3 washings, 50 μL/well anti-phosphotyrosine Ab PY20(AP) labeled with alkaline phosphatase (Zymed) diluted to 0.2 μg/mL in blocking buffer is added and incubated over night (4° C.). For all incubation steps the plates are covered with plate sealers (Costar). Finally, the plates are washed another three times with washing buffer and once with deionized water before addition of 90 μL/well of the AP-substrate CDPStar RTU with Emerald II. The plates, now sealed with Packard TopSeal™-A plate sealers, are incubated for 45 min at room temperature in the dark and luminescence is quantified by measuring counts per second (CPS) with a Packard Top Count Microplate Scintillation Counter (Top Count). The difference between the ELI SA-readout (CPS) obtained for with the lysates of the untreated 32D-Bcr/Abl cells and the readout for the assay-background (all components, but without cell lysate) is calculated and taken as 100% reflecting the constitutively phosphorylated Bcr-Abl protein present in these cells. The activity of the compound on the Bcr-Abl kinase activity is expressed as percent reduction of the Bcr-Abl phosphorylation. The values for the $IC_{50}$ and $IC_{90}$ are determined from the dose response curves by graphical extrapolation.

Test for activity against VEGF-receptor tyrosine kinase. The test is conducted using Flt-1 VEGF-receptor tyrosine kinase. The detailed procedure is as follows: 30 μL kinase solution (10 ng of the kinase domain of Flt-1, Shibuya et al., Oncogene 5, 519-24 [1990]) in 20 mM Tris.HCl pH 7.5, 3 mM manganese dichloride ($MnCl_2$), 3 mM magnesium chloride ($MgCl_2$), 10 μM sodium vanadate, 0.25 mg/mL polyethylenglycol (PEG) 20000, 1 mM dithiothreitol and 3 μg/μL poly(Glu, Tyr) 4:1 (Sigma, Buchs, Switzerland), 8 μM [$^{33}$P]-ATP (0.2 μCi), 1% DMSO, and 0 to 100 μM of the compound to be tested are incubated together for 10 minutes at room temperature. The reaction is then terminated by the addition of 10 μL 0.25 M ethylenediaminetetraacetate (EDTA) pH 7. Using a multichannel dispenser (LAB SYSTEMS, USA), an aliquot of 20 μL is applied to a PVDF (=polyvinyl difluoride) Immobilon P membrane (Millipore, Bedford, USA), through a Gibco-BRL microtiter filter manifold and connected to a vacuum. Following complete elimination of the liquid, the membrane is washed 4 times successively in a bath containing 0.5% phosphoric acid ($H_3PO_4$) and once with ethanol, incubated for 10 minutes each time while shaking, then mounted in a Hewlett Packard TopCount Manifold and the radioactivity measured after the addition of 10 μL Microscint® (β-scintillation counter liquid). $IC_{50}$-values are determined by linear regression analysis of the percentages for the inhibition of each compound in at least four concentrations (as a rule 0.01, 0.1, 1.0 and 10 μmol). The $IC_{50}$-values that can be found with compounds of formula I are in the range of 1 to 10'000 nM, preferably in the range of 1 to 100 nM.

The inhibition of VEGF-induced KDR-receptor autophosphorylation can be confirmed with a further in vitro experiment in cells: transfected CHO cells, which permanently express human VEGF receptor (KDR), are seeded in complete culture medium with 10% fetal calf serum (FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/mL). After a further five minute incubation at 37° C., the cells are washed twice with ice-cold PBS (phosphate-buffered saline) and immediately lysed in 100 μL lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the KDR-receptor phosphorylation: a monoclonal antibody to KDR (for example Mab 1495.12.14) is immobilized on black ELISA plates (OptiPlate™ HTRF-96 from Packard). The plates are then washed and the remaining free protein-binding sites are saturated with 1% BSA in PBS. The cell lysates (20 μg protein per well) are then incubated in these plates overnight at 4° C. together with an anti-phosphotyrosine antibody coupled with alkaline phosphatase (PY20:AP from Transduction Laboratories). The plates are washed again and the binding of the antiphosphotyrosine antibody to the captured phosphorylated receptor is then demonstrated using a luminescent AP substrate (CDP-Star, ready to use, with Emerald II; TROPIX). The luminescence is measured in a Packard Top Count Microplate Scintillation Counter (Top Count). The difference between the signal of the positive control (stimulated with VEGF) and that of the negative control (not stimulated with VEGF) corresponds to VEGF-induced KDR-receptor phosphorylation (=100%). The activity of the tested substances is calculated as % inhibition of VEGF-induced KDR-receptor phosphorylation, wherein the concentration of substance that induces half the maximum inhibition is defined as the ED50 (effective dose for 50% inhibition). Compounds of formula I here preferably show ED50 values in the range of 0.25 nM to 1000 nM, preferably 0.25 to 250 nM.

A compound of formula I or a N-oxide thereof inhibits to varying degrees also other tyrosine kinases involved in signal transduction which are mediated by trophic factors, for example Bcr-Abl and Abl kinase, Arg, kinases from the Src family, especially c-Src kinase, Lck, and Fyn; also kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase; and also serine/threonine kinases, all of which play a role in growth regulation and transformation in mammalian cells, including human cells.

The inhibition of c-erbB2 tyrosine kinase (HER-2) can be measured, for example, in the same way as the inhibition of EGF-R protein kinase, using known procedures.

On the basis of these studies, a compound of formula I according to the invention shows therapeutic efficacy especially against disorders dependent on protein kinase, especially proliferative diseases.

On the basis of their efficacy as inhibitors of VEGF-receptor tyrosine kinase activity, the compounds of the formula I primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, hemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, diabetes, endometriosis, chronic asthma, and especially neoplastic diseases (solid tumors, but also leukemia's and other "liquid tumors", especially those expressing c-kit, KDR, Flt-1 or Flt-3), such as especially breast cancer, cancer of the colon, lung cancer (especially small-cell lung cancer), cancer of the prostate or Kaposi's sarcoma. A compound of formula I (or an N-oxide thereof) inhibits the growth of tumors and is especially suited to preventing the metastatic spread of tumors and the growth of micrometastases.

A compound of formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula I can besides or in addition be administered especially for tumor therapy, such as leukaemia therapy, in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Therapeutic agents for possible combination are especially one or more cytostatic or cytotoxic compounds, for example a chemotherapeutic agent or several selected from the group comprising idarubicin, cytarabine, interferon, hydroxyurea, bisulfan, or an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, and an inhibitor of the interaction of an SH2 domain with a phosphorylated protein.

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

In general, the invention relates also to the use of a compound of formula I or a N-oxide thereof for the inhibition of tyrosine kinase activity, either in vitro or in vivo.

With the groups of preferred compounds of formula I and N-oxides thereof mentioned hereinafter, definitions of substituents from the general definitions mentioned hereinbefore may reasonably be used, for example, to replace more general definitions with more specific definitions or especially with definitions characterized as being preferred.

In particular, the invention relates to compounds of formula I, wherein $R_1$, represents hydrogen, lower alkyl, lower alkoxy-lower alkyl, acyloxy-lower alkyl, carboxy-lower alkyl, lower alkoxycarbonyl-lower alkyl, or phenyl-lower alkyl;

$R_2$ represents hydrogen, lower alkyl, optionally substituted by one or two identical or different radicals $R_3$, cycloalkyl, benzcycloalkyl, heterocyclyl, an aryl group, or a mono- or bicyclic heteroaryl group comprising one, two or three nitrogen atoms or one sulfur atom, which aryl and heteroaryl groups in each case are unsubstituted or mono- or polysubstituted;

and $R_3$ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, furanyl, thienoyl, or a mono- or bicyclic heteroaryl group comprising one, two or three ring nitrogen atoms, zero or one ring oxygen atom and zero or one ring sulphur atom, which aryl and heteroaryl groups in each case are unsubstituted or mono- or polysubstituted;

or wherein $R_1$ and $R_2$ together represent alkylene with four or five carbon atoms, optionally mono- or disubstituted by lower alkyl, cycloalkyl, heterocyclyl, phenyl, hydroxy, lower alkoxy, amino, mono- or disubstituted amino, pyridyl, pyrazinyl or pyrimidinyl; benzalkylene with four or five carbon atoms in the alkylene group; oxaalkylene with one oxygen and three or four carbon atoms, or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, phenyl, substituted phenyl, pyridinyl, pyrimidinyl, or pyrazinyl;

R₄ represents hydrogen, lower alkyl, or halogen;
and a N-oxide or a pharmaceutically acceptable salt of such a compound.

More particular, the invention relates to compounds of formula I, wherein
R₁ represents hydrogen, lower alkyl, lower alkoxy-lower alkyl, lower alkoxycarbonyl-lower alkyl, or phenyl-lower alkyl;
R₂ represents hydrogen, lower alkyl, optionally substituted by one or two identical or different radicals R₃, cyclopentyl, benzcyclopentyl, cyclohexyl, pyrrolidinyl, oxazolinyl, piperidinyl, N-substituted piperidinyl, morpholinyl, azepinyl, oxo-azepinyl, oxazepinyl, phenyl, naphthalenyl, tetrahydronaphthalinyl or a mono- or bicyclic heteroaryl group comprising one or two nitrogen atoms, which phenyl, naphthalenyl and heteroaryl groups in each case are unsubstituted or mono- or polysubstituted, thienyl, or lower alkoxycarbonyl-lower alkylthienyl;
and R₃ represents hydroxy, lower alkoxy, acyloxy, carboxy, lower alkoxycarbonyl, carbamoyl, N-mono- or N,N-disubstituted carbamoyl, amino, lower alkylamino, di-lower alkylamino, phenylamino, N-lower alkyl-N-phenylamino, pyrrolidino, oxopyrrolidino, piperidino, morpholino, imidazolino, oxoimidazolino, cycloalkyl, heterocyclyl, furyl; phenyl, naphthalenyl, tetrahydronaphthalinyl, or a mono- or bicyclic heteroaryl group comprising one or two nitrogen atoms, which phenyl, naphthalenyl and heteroaryl group are unsubstituted or mono- or polysubstituted;
or wherein R₁ and R₂ together represent alkylene with four or five carbon atoms, optionally mono- or disubstituted by lower alkyl, cycloalkyl, heterocyclyl, phenyl, hydroxy, lower alkoxy, amino, mono- or disubstituted amino, pyridyl, pyrazinyl or pyrimidinyl; benzalkylene with four or five carbon atoms in the alkylene group; oxaalkylene with one oxygen and four carbon atoms; or azaalkylene with one nitrogen and four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, phenyl, substituted phenyl, pyridinyl, pyrimidinyl, or pyrazinyl;
R₄ represents hydrogen, lower alkyl, or halogen;
and a N-oxide or a pharmaceutically acceptable salt of such a compound.

More particular, the invention relates to compounds of formula I, wherein
R₁ represents hydrogen, lower alkyl, lower alkoxy-lower alkyl, lower alkoxycarbonyl-lower alkyl, or phenyl-lower alkyl;
R₂ represents hydrogen; lower alkyl, optionally substituted by one radical R₃, by two phenyl groups, by two lower alkoxycarbonyl groups, by phenyl and lower alkoxycarbonyl, or by hydroxyphenyl and lower alkoxycarbonyl; cyclopentyl; benzcyclopentyl; cyclohexyl; pyrrolidinyl; oxazolinyl; piperidinyl; N-lower alkylpiperidinyl; N-benzylpiperidinyl; N-pyrimidinylpiperidinyl; morpholinyl; azepinyl; oxo-azepinyl; oxazepinyl; phenyl, naphthalinyl, tetrahydronaphthalinyl or a mono- or bicyclic heteroaryl group comprising one or two nitrogen atoms, which phenyl, naphthalenyl and heteroaryl groups in each case are unsubstituted or substituted by one or two substituents selected from the group consisting of lower alkyl, trifluoro-lower alkyl, hydroxy-lower alkyl, lower alkoxy-lower alkyl, amino-lower alkyl, lower alkylamino-lower alkyl, di-lower alkylamino-lower alkyl, N-cyclohexyl-N-lower alkylamino-lower alkyl, lower alkoxycarbonylpiperidino-lower alkyl, N-lower alkylpiperazino-lower alkyl, lower alkoxycarbonyl-lower alkyl, hydroxy, lower alkoxy, trifluoro-lower alkoxy, 1H-imidazolyl-lower alkoxy, lower alkanoyloxy, benzoyloxy, carboxy, lower alkoxycarbonyl, carbamoyl, lower alkyl carbamoyl, amino, lower alkanoylamino, benzoylamino, amino mono- or disubstituted by lower alkyl, by hydroxy-lower alkyl or by lower alkoxy-lower alkyl, 1H-imidazolyl, mono- or di-lower alkyl-1H-imidazolyl, pyrrolidino, piperidino, piperazino, N-lower alkylpiperazino, morpholino, sulfamoyl, lower alkylsulfonyl, phenylsulfonyl, lower alkylsulfinyl, phenylsulfinyl, lower alkylthio, phenylthio, phenyl, pyridyl, halogenyl, or benzoyl; thienyl; or lower alkoxycarbonyl-lower alkylthienyl; and
R₃ represents hydroxy, lower alkoxy, acyloxy, carboxy, lower alkoxycarbonyl, carbamoyl, carbamoyl mono- or disubstituted by lower alkyl, phenyl or lower alkylene, amino, lower alkylamino, di-lower alkylamino, phenylamino, N-lower alkyl-N-phenylamino, pyrrolidino, oxopyrrolidino, piperidino, morpholino, imidazolino, oxoimidazolino, cycloalkyl, heterocyclyl, furyl; phenyl, naphthalenyl, tetrahydronaphthalinyl, or a mono- or bicyclic heteroaryl group comprising one or two nitrogen atoms, which phenyl, naphthalenyl and heteroaryl group is unsubstituted or substituted by one or two substituents selected from the group consisting of lower alkyl, trifluoro-lower alkyl, lower alkoxycarbonyl-lower alkyl, hydroxy, lower alkoxy, trifluoro-lower alkoxy, lower alkanoyloxy, benzoyloxy, carboxy, lower alkoxycarbonyl, carbamoyl, amino, lower alkanoylamino, benzoylamino, amino mono- or disubstituted by lower alkyl, by hydroxy-lower alkyl or by loweralkoxy-lower alkyl, pyrrolidino, piperidino, morpholino, piperazino, N-lower alkylpiperazino, N-lower alkoxycarbonylpiperazino, phenyl, pyridyl, 1H-imidazolyl, lower alkyl-1H-imidazolyl, sulfamoyl, lower alkylsulfonyl, phenylsulfonyl, lower alkylsulfinyl, phenylsulfinyl, lower alkylthio, phenylthio, halogenyl, or benzoyl;
or wherein R₁ and R₂ together represent alkylene with four or five carbon atoms, optionally mono- or disubstituted by lower alkyl, cycloalkyl, phenyl, hydroxy, lower alkoxy, amino, benzoylamino, piperidino, pyridyl, pyrazinyl or pyrimidinyl; benzalkylene with four or five carbon atoms in the alkylene group; oxaalkylene with one oxygen and four carbon atoms; or azaalkylene with one nitrogen and four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, carbamoyl-lower alkyl N-mono- or N,N-disubstituted by lower alkyl, phenyl, lower alkylene or oxa-lower alkylene, cycloalkyl, lower alkoxycarbonyl, phenyl, methoxyphenyl, trifluoromethylphenyl, trifluoromethoxyphenyl, pyridinyl, pyrimidinyl, or pyrazinyl;
R₄ represents hydrogen or lower alkyl;
and a N-oxide or a pharmaceutically acceptable salt of such a compound.

In a preferred group of compounds of formula I,
R₁ represents hydrogen, lower alkyl, lower alkoxy-lower alkyl, or benzyl;
R₂ represents lower alkyl, optionally substituted by one radical R₃, by two phenyl groups, by two lower alkokycarbonyl groups, by phenyl and lower alkoxycarbonyl, or by hydroxyphenyl and lower alkoxycarbonyl; cyclopentyl; benzcyclopentyl; cyclohexyl; pyrrolidinyl; piperidinyl; N-lower alkylpiperidinyl; N-benzylpiperidinyl; N-pyrimidinylpiperidinyl; morpholinyl; azepinyl; oxoazepinyl; phenyl; naphthalenyl; tetrahydronaphthalinyl; pyridyl; lower alkyl-pyridyl; quinolinyl; thienyl; lower alkoxycarbonylmethylthienyl; or phenyl substituted by one or two substituents selected from the group consisting of lower alkyl, trifluoro-lower alkyl, hydroxy-lower alkyl, amino-lower alkyl, lower alkylamino-lower alkyl, di-lower alkylamino-lower alkyl, N-cyclohexyl-N-lower alkylamino-lower alkyl, lower alkoxycarbonylpiperidino-lower alkyl, N-lower alkylpiperazino-lower alkyl, lower alkoxycarbonyl-lower alkyl, hydroxy, lower alkoxy, trifluoro-lower alkoxy, 1H-imidazolyl-lower alkoxy, lower alkanoyloxy, benzoyloxy, carboxy, lower alkoxycarbonyl, carbamoyl, lower alkylcarbamoyl, amino, lower alkanoylamino, benzoylamino, amino mono- or disubstituted by lower alkyl, by hydroxy-lower alkyl or by loweralkoxy-lower alkyl, 1H-imidazolyl, lower alkyl-1H-imidazolyl, pyrrolidino, piperidino, piperazino, N-lower alkylpiperazino, morpholino, sulfamoyl, lower alkylsulfonyl, phenyl, pyridyl, halogenyl, or benzoyl;

and $R_3$ represents hydroxy, lower alkoxy, lower alkanoyloxy, benzoyloxy, carboxy, lower alkoxycarbonyl, carbamoyl, amino, lower alkylamino, di-lower alkylamino, phenylamino, N-lower alkyl-N-phenylamino, pyrrolidino, oxopyrrolidino, piperidino, morpholino, imidazolino, oxoimidazolino, cyclopropyl, cyclopentyl, cyclohexyl, tetrahydrofuranyl, phenyl, naphthalenyl, tetrahydronaphthalinyl, furyl, a mono- or bicyclic heteroaryl group comprising one or two nitrogen atoms, which heteroaryl group is unsubstituted or mono- or disubstituted by lower alkyl, hydroxy and lower alkoxy, or phenyl substituted by one or two substituents selected from the group consisting of lower alkyl, trifluoro-lower alkyl, lower alkoxycarbonyl-lower alkyl, hydroxy, lower alkoxy, trifluoro-lower alkoxy, lower alkanoyloxy, benzoyloxy, carboxy, lower alkoxycarbonyl, carbamoyl, amino, lower alkanoylamino, benzoylamino, amino mono- or disubstituted by lower alkyl, by hydroxy-lower alkyl or by loweralkoxy-lower alkyl, pyrrolidino, piperidino, morpholino, piperazino, N-lower alkylpiperazino, N-lower alkoxycarbonylpiperazino, phenyl, pyridyl, 1H-imidazolyl, lower alkyl-1H-imidazolyl, sulfamoyl, lower alkylsulfonyl, halogenyl, or benzoyl;

or wherein $R_1$ and $R_2$ together represent alkylene with four or five carbon atoms, optionally mono- or disubstituted by phenyl, hydroxy, amino, benzoylamino, or piperidino; benzalkylene with four or five carbon atoms in the alkylene group; oxaalkylene with one oxygen and four carbon atoms; or azaalkylene with one nitrogen and four carbon atoms wherein nitrogen is unsubstituted or substituted by lower alkyl, phenyl-lower alkyl, lower alkoxycarbonyl-lower alkyl, carbamoyl-lower alkyl, pyrrolidinocarbonyl-lower alkyl, morpholinocarbonyl-lower alkyl, cyclopentyl, lower alkoxycarbonyl, phenyl, methoxyphenyl, trifluoromethylphenyl, pyridinyl; pyrimidinyl, or pyrazinyl;

$R_4$ represents hydrogen or methyl;

and a N-oxide or a pharmaceutically acceptable salt of such a compound.

A specially preferred group of compounds comprises compounds of formula I wherein $R_1$ represents hydrogen, and $R_2$ represents phenyl substituted by trifluoromethyl, especially 3-trifluoromethylphenyl, and optionally a further substituent selected from the group consisting of hydroxy-lower alkyl, e.g. 1-hydroxy-1-methylethyl, lower alkylamino, e.g. methyl- or ethylamino, hydroxy-lower alkylamino, e.g. 2-hydroxy-1-propylamino or 2-hydroxy-2-propylamino, di-lower alkylamino, e.g. diethylamino, 1H-imidazolyl, lower alkyl-1H-imidazolyl, e.g. 2- or 4-methyl-1H-imidazolyl, carbamoyl, lower alkylcarbamoyl, e.g. methylcarbamoyl, pyrrolidino, piperidino, piperazino, lower alkylpiperazino, e.g. 4-methylpiperazino, morpholino, lower alkoxy, e.g. methoxy, fluoro-lower alkoxy, e.g. trifluoromethoxy or 2,2,2-trifluoroethoxy, phenyl, pyridyl, e.g. 2-, 3- or 4-pyridyl, and halogenyl, e.g. chloro or fluoro;

$R_4$ represents methyl;

and a N-oxide or a pharmaceutically acceptable salt of such a compound.

One preferred embodiment of the invention relates to compounds of formula I wherein $R_1$ is hydrogen, $R_2$ represents phenyl which is mono- or disubstituted by imidazol-lower alkoxy, lower alkyl amino, trifluoromethyl, hydroxy lower alkyl amino, bis-(lower alkoxy lower alkyl) amino, lower alkyl piperazinyl, piperidinyl, pyrrolidinyl, morpholinyl, phenyl, pyridyl, imidazolyl which is unsubstituted or mono or disubstituted by lower alkyl or N-lower alkyl carbamoyl;

$R_4$ is lower alkyl;

and to the N-oxides and pharmaceutically acceptable salts of such compounds.

Particularly preferred are the compounds of the Examples. Other compounds which are particularly preferred are:

4-Methyl-3-[[4-(3-pyridinyl)-2-pyrimidinyl]amino]benzamide,

4-Methyl-3-[[4-(3-pyridinyl)-2-pyrimidinyl]amino]benzanilide,

4-Methyl-N-(3-pyridinyl)-3-[[4-(3-pyridinyl)-2-pyrimidinyl]amino]benzamide,

N-(4-Chlorophenyl)-4-methyl-3-[[4-(3-pyridinyl)-2-pyrimidinyl]amino]benzamide,

2(R)— and 2(S)-[4-methyl-3-[[4-(3-pyridinyl)-2-pyrimidinyl]amino]benzoylamino]propanoic acid, 4-Methyl-3-[[4-(3-pyridinyl)-2-pyrimidinyl]amino]-N-(8-quinolinyl)benzamide, 4-Methyl-3-[[4-(3-pyridinyl)-2-pyrimidinyl]amino]-N-(3-[trifluoromethoxy]phenyl)benzamide, 4-Methyl-3-[[4-(3-pyridinyl)-2-pyrimidinyl]amino]-N-(2-pyrrolidinoethyl)benzamide, 4-Methyl-3-[[4-(3-pyridinyl)-2-pyrimidinyl]amino]-N-(3-pyrrolidinophenyl)benzamide, 4-Methyl-3-[[4-(3-pyridinyl)-2-pyrimidinyl]amino]-N-(1-[2-pyrimidinyl]-4-piperidinyl)benzamide, N-(4-Di-[2-methoxyethyl]amino-3-trifluoromethylphenyl)-4-methyl-3-[[4-(3-pyridinyl)-2-pyrimidinyl]amino]benzamide, N-(4-[1H-Imidazolyl]-3-trifluoromethylphenyl)-4-methyl-3-[[4-(3-pyridinyl)-2-pyrimidinyl]amino]benzamide, 4-Methyl-3-[[4-(3-pyridinyl)-2-pyrimidinyl]amino]-N-(2-pyrrolidino-5-trifluoromethylphenyl)benzamide, N-(3,4-difluorophenyl)-4-methyl-3-[[4-(3-pyridinyl)-2-pyrimidinyl]amino]benzamide, 4-Methyl-3-[[4-(3-pyridinyl)-2-pyrimidinyl]amino]-N-(3-trifluoromethylbenzyl)benzamide, 4-Methyl-3-[[4-(3-pyridinyl)-2-pyrimidinyl]amino]-N-(3-trifluoromethylphenyl)benzamide, N-(3-Chloro-5-trifluoromethylphenyl)-4-methyl-3-[[4-(3-pyridinyl)-2-pyrimidinyl]amino]benzamide, N-(4-Dimethylaminobutyl)-4-methyl-3-[[4-(3-pyridinyl)-2-pyrimidinyl]amino]benzamide, 4-Methyl-N-[4-(4-methyl-1-piperazinyl)-3-trifluoromethylphenyl]-3-[[4-(3-pyridinyl)-2-pyrimidinyl]amino]benzamide, 4-Methyl-3-[[4-(3-pyridinyl)-2-pyrimidinyl]amino]-N-[4-(2,2,2-trifluoroethoxy)-3-trifluoromethylphenyl]benzamide, 4-Methyl-N-[4-(2-methyl-1H-imidazolyl)-3-trifluoromethylphenyl]-3-[[4-(3-pyridinyl)-2-pyrimidinyl]amino]benzamide,
4-Methyl-N-(4-phenyl-3-trifluoromethylphenyl)-3-[[4-(3-pyridinyl)-2-pyrimidinyl]amino]benzamide,
4-Methyl-N-[4-(4-methyl-1H-imidazolyl)-3-trifluoromethylphenyl]-3-[[4-(3-pyridinyl)-2-pyrimidinyl]amino]benzamide,
Methyl 2(R)- and 2(S)-[4-methyl-3-[[4-(3-pyridinyl)-2-pyrimidinyl]amino]benzoylamino]-3-[4-hydroxyphenyl]propanoate,
N-[2-(N-Cyclohexyl-N-methylaminomethyl)phenyl]-4-methyl-3-[[4-(3-pyridinyl)-2-pyrimidinyl]amino]benzamide,
N-[3-[2-(1H-Imidazolyl)ethoxy]phenyl]-4-methyl-3-[[4-(3-pyridinyl)-2-pyrimidinyl]amino]benzamide,
4-Methyl-N-[3-morpholino-5-trifluoromethylphenyl]-3-[[4-(3-pyridinyl)-2-pyrimidinyl]amino]benzamide,
4-Methyl-3-[[4-(3-pyridinyl)-2-pyrimidinyl]amino]-N-(4-pyrrolidino-3-trifluoromethylphenyl)benzamide,
4-Methyl-3-[[4-(3-pyridinyl)-2-pyrimidinyl]amino]-N-(4-piperidino-3-trifluoromethylphenyl)benzamide,
4-Methyl-N-[4-morpholino-3-trifluoromethylphenyl]-3-[[4-(3-pyridinyl)-2-pyrimidinyl]amino]benzamide,
N-(4-Ethylamino-3-trifluoromethylphenyl)-4-methyl-3-[[4-(3-pyridinyl)-2-pyrimidinyl]amino]benzamide,
4-Methyl-3-[[4-(3-pyridinyl)-2-pyrimidinyl]amino]-N-(3-trifluoromethoxyphenyl)benzamide,
N-[4-(2-Hydroxypropylamino)-3-trifluoromethylphenyl]-4-methyl-3-[[4-(3-pyridinyl)-2-pyrimidinyl]amino]benzamide,
N-(4-Diethylamino-3-trifluoromethylphenyl)-4-methyl-3-[[4-(3-pyridinyl)-2-pyrimidinyl]amino]benzamide,
4-Methyl-3-[[4-(3-pyridinyl)-2-pyrimidinyl]amino]-N[3-(3-pyridinyl)-5-trifluorophenyl]benzamide,
N-[3-[3-(1H-Imidazolyl)propoxy]phenyl]-4-methyl-3-[[4-(3-pyridinyl)-2-pyrimidinyl]amino]benzamide,
4-Methyl-3-[[4-(3-pyridinyl)-2-pyrimidinyl]amino]-N-[4-(3-pyridinyl)-3-trifluorophenyl]benzamide,
4-Methyl-N-[3-(4-methyl-1-piperazinyl)-5-trifluorophenyl]-3-[[4-(3-pyridinyl)-2-pyrimidinyl]amino]benzamide,
4-Methyl-N-[3-methylcarbamoyl-5-trifluorophenyl]-3-[[4-(3-pyridinyl)-2-pyrimidinyl]amino]benzamide,
4-Methyl-N-[3-methylcarbamoyl-5-morpholino]-3-[[4-(3-pyridinyl)-2-pyrimidinyl]amino]benzamide.
Further compounds which are particularly preferred are:
4-Methyl-3-[[4-(3-pyridinyl)-2-pyrimidinyl]amino]-N-[3-[3-(1H-imidazol-1-yl)propoxy]-phenyl]benzamide,
4-Methyl-3-[[4-(3-pyridinyl)-2-pyrimidinyl]amino]-N-[3-[2-(1H-imidazol-1-yl)ethoxy]phenyl]benzamide,
4-Methyl-3-[[4-(3-pyridinyl)-2-pyrimidinyl]amino]-N-[4-(ethylamino)-3-(trifluoromethyl)phenyl]benzamide,
4-Methyl-3-[[4-(3-pyridinyl)-2-pyrimidinyl]amino]-N-[4-(diethylamino)-3-(trifluoromethyl)phenyl]benzamide,
(±)-4-Methyl-3-[[4-(3-pyridinyl)-2-pyrimidinyl]amino]-N-[4-[(2-hydroxypropyl)amino]-3-(trifluoromethyl)phenyl]benzamide,
4-Methyl-3-[[4-(3-pyridinyl)-2-pyrimidinyl]amino]-N-[4-[bis(2-methoxyethyl)amino]-3-(trifluoromethyl)phenyl]benzamide,
4-Methyl-3-[[4-(3-pyridinyl)-2-pyrimidinyl]amino]-N-[4-(4-methyl-1-piperazinyl)-3-(trifluoromethyl)phenyl]benzamide,
4-Methyl-3-[[4-(3-pyridinyl)-2-pyrimidinyl]amino]-N-[4-(1-piperidinyl)-3-(trifluoromethyl)phenyl]benzamide,
4-Methyl-3-[[4-(3-pyridinyl)-2-pyrimidinyl]amino]-N-[4-(1-pyrrolidinyl)-3-(trifluoromethyl)phenyl]benzamide,
4-Methyl-3-[[4-(3-pyridinyl)-2-pyrimidinyl]amino]-N-[4-(4-morpholinyl)-3-(trifluoromethyl)phenyl]benzamide,
4-Methyl-3-[[4-(3-pyridinyl)-2-pyrimidinyl]amino]-N-[4-phenyl-3-(trifluoromethyl)phenyl]benzamide,
4-Methyl-3-[[4-(3-pyridinyl)-2-pyrimidinyl]amino]-N-[3-[4-(3-pyridinyl)-3-(trifluoromethyl)phenyl]methyl]benzamide,
4-Methyl-3-[[4-(3-pyridinyl)-2-pyrimidinyl]amino]-N-[4-(1H-imidazol-1-yl)-3-(trifluoromethyl)phenyl]benzamide,
4-Methyl-3-[[4-(3-pyridinyl)-2-pyrimidinyl]amino]-N-[4-(2,4-dimethyl-1H-imidazol-1-yl)-3-(trifluoromethyl)phenyl]benzamide,
4-Methyl-3-[[4-(3-pyridinyl)-2-pyrimidinyl]amino]-N-[4-(4-methyl-1H-imidazol-1-yl)-3-(trifluoromethyl)phenyl]benzamide,
4-Methyl-3-[[4-(3-pyridinyl)-2-pyrimidinyl]amino]-N-[4-(2-methyl-1H-imidazol-1-yl)-3-(trifluoromethyl)phenyl]benzamide,
4-Methyl-3-[[4-(3-pyridinyl)-2-pyrimidinyl]amino]-N-[3-(4-morpholinyl)-5-[(methylamino)carbonyl]phenyl]benzamide,
4-Methyl-3-[[4-(3-pyridinyl)-2-pyrimidinyl]amino]-N-[3-[(methylamino)carbonyl]-5-(trifluoromethyl)phenyl]benzamide,
4-Methyl-3-[[4-(3-pyridinyl)-2-pyrimidinyl]amino]-N-[5-(3-pyridinyl)-3-(trifluoromethyl)phenyl]benzamide,
4-Methyl-3-[[4-(3-pyridinyl)-2-pyrimidinyl]amino]-N-[5-(4-morpholinyl)-3-(trifluoromethyl)phenyl]benzamide,
4-Methyl-3-[[4-(3-pyridinyl)-2-pyrimidinyl]amino]-N-[5-(2-methyl-1H-imidazol-1-yl)-3-(trifluoromethyl)phenyl]benzamide,
4-Methyl-3-[[4-(3-pyridinyl)-2-pyrimidinyl]amino]-N-[5-(4-methyl-1H-imidazol-1-yl)-3-(trifluoromethyl)phenyl]benzamide,
4-Methyl-3-[[4-(3-pyridinyl)-2-pyrimidinyl]amino]-N-[5-(5-methyl-1H-imidazol-1-yl)-3-(trifluoromethyl)phenyl]benzamide,
4-Methyl-3-[[4-(3-pyridinyl)-2-pyrimidinyl]amino]-N-[3-(4-methyl-1-piperazinyl)-5-(trifluoromethyl)phenyl]benzamide, and
4-Methyl-3-[[4-(3-pyridinyl)-2-pyrimidinyl]amino]-N-[2-(1-pyrrolidinyl)-5-(trifluoromethyl)phenyl]benzamide.

The invention relates also to 4-methyl-3-[[4-(3-pyridinyl)-2-pyrimidinyl]amino]benzoic acid and to 3-[[4-(3-pyridinyl)-2-pyrimidinyl]amino]benzoic acid; intermediates for the formation of the preferred amides of the invention.

Especially, the invention relates to the use of a compound of formula I or of a N-oxide or a possible tautomer thereof or of a pharmaceutically acceptable salt of such a compound for the preparation of a pharmaceutical composition for the treatment of a disease which responds to an inhibition of protein kinase activity, wherein the disease is a neoplastic disease.

More particularly, the invention relates to the use of a compound of the formula I or of a N-oxide or a possible tautomer thereof; or of a pharmaceutically acceptable salt of such a compound for the preparation of a pharmaceutical composition for the treatment of leukaemia which responds to an inhibition of the Abl tyrosine kinase activity.

Furthermore, the invention provides a method for the treatment of a disease which responds to an inhibition of protein kinase activity, which comprises administering a compound of formula I or a N-oxide or a pharmaceutically acceptable salt thereof, wherein the radicals and symbols have the meanings as defined above, in a quantity effective against said disease, to a warm-blooded animal requiring such treatment.

A compound of the invention may be prepared by processes that, though not applied hitherto for the new compounds of the present invention, are known per se, especially a process characterized in that for the synthesis of a compound of the formula I wherein the symbols $R_1$, $R_2$ and $R_4$ are as defined for a compound of the formula I, a 4-$R_4$-3-[[4-(3-pyridinyl)-2-pyrimidinyl]amino]-benzoic acid of formula II

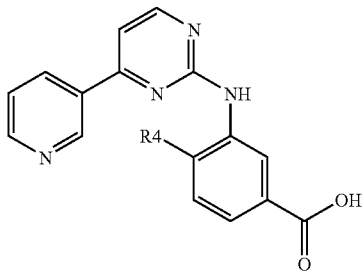

wherein $R_4$ is as defined for a compound of formula I, or a derivative thereof wherein the carboxy group —COOH is in activated form, is reacted with an amine of the formula III

wherein $R_1$ and $R_2$ are as defined for a compound of the formula I, optionally in the presence of a dehydrating agent and an inert base and/or a suitable catalyst, and optionally in the presence of an inert solvent;

where the above starting compounds II and III may also be present with functional groups in protected form if necessary and/or in the form of salts, provided a salt-forming group is present and the reaction in salt form is possible;

any protecting groups in a protected derivative of a compound of the formula I are removed; and, if so desired, an obtainable compound of formula I is converted into another compound of formula I or a N-oxide thereof, a free compound of formula I is converted into a salt, an obtainable salt of a compound of formula I is converted into the free compound or another salt, and/or a mixture of isomeric compounds of formula I is separated into the individual isomers.

Detailed Description of the Process:

A derivative of the compound of formula II wherein the carboxy group is in activated form is especially a reactive ester, a reactive anhydride or a reactive cyclic amide.

Reactive esters of the acid of formula II are especially esters unsaturated at the linking carbon atom of the esterifying radical, for example esters of the vinyl ester type, such as actual vinyl esters (obtainable, for example, by transesterification of a corresponding ester with vinyl acetate; activated vinyl ester method), carbamoylvinyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonyl-phenol, 2,4,5-trichlorophenol, 2,3,4,5,6-pentachlorophenol or 4-phenyl-diazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thio esters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), amino or amido esters (obtainable, for example, by treatment of the corresponding acid with an N-hydroxy-amino or N-hydroxy-amido compound, for example N-hydroxy-succinimide, N-hydroxy-piperidine, N-hydroxy-phthalimide or 1-hydroxy-benzotriazole, for example by the anhydride or carbodiimide method; activated N-hydroxy esters method), or silyl esters (which are obtainable, for example, by treatment of the corresponding acid with a silylating agent, for example hexamethyl disilazane, and react readily with hydroxy groups but not with amino groups).

Anhydrides of the acid of formula II may be symmetric or preferably mixed anhydrides of that acid, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment thereof with nitrous acid; azide method), anhydrides with carbonic acid semiderivatives, such as corresponding esters, for example carbonic acid lower alkyl semiesters (obtainable, for example, by treatment of the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), or anhydrides with organic acids, such as mixed anhydrides with organic carboxylic acids (obtainable, for example, by treatment of the corresponding acid with an unsubstituted or substituted lower alkane- or phenylalkane-carboxylic acid halide, for example phenylacetic acid chloride, pivalic acid chloride or trifluoroacetic acid chloride; mixed carboxylic acid anhydrides method), with organic sulfonic acids (obtainable, for example, by treatment of a salt, such as an alkali metal salt, of the corresponding acid, with a suitable organic sulfonic acid halide, such as lower alkane- or aryl-, for example methane- or p-toluene-sulfonic acid chloride; mixed sulfonic acid anhydrides method), or with organic phosphonic acids (obtainable, for example, by treatment of the corresponding acid with a suitable organic phosphonic anhydride or phosphonic cyanide; mixed phosphonic acid anhydrides method), and symmetric anhydrides (obtainable, for example, by condensation of the corresponding acid in the presence of a carbodiimide or of 1-diethylaminopropyne; symmetric anhydrides method).

Suitable cyclic amides are especially amides with five-membered diazacycles of aromatic character, such as amides with imidazoles, for example imidazole (obtainable, for example, by treatment of the corresponding acid with N,N'-carbonyldiimidazole; imidazolide method), or pyrazoles, for example 3,5-dimethyl-pyrazole (obtainable, for example, by way of the acid hydrazide by treatment with acetylacetone; pyrazolide method).

Derivatives of the acid of formula II wherein the carboxy group is in activated form are preferably formed in situ. For example, N,N'-disubstituted amidino esters can be formed in situ by reacting a mixture of the acid of formula II and the amine of formula III in the presence of a suitable N,N-disubstituted carbodiimide, for example N,N'-dicyclohexylcarbodiimide. Reactive mixed anhydrides of the acid of formula II with an organic phosphonic acid may be formed in situ by reaction with e.g. propylphosphonic anhydride or diethylcyanophosphonate in the presence of suitable base, preferably a tertiary amine, e.g. triethylamine or dimethylaminopyridine.

The reaction can be carried out in a manner known per se, the reaction conditions being dependent especially on whether, and if so how, the carboxy group of the carboxylic acid of formula II has been activated, usually in the presence of a suitable solvent or diluent or of a mixture thereof and, if necessary, in the presence of a condensation agent, which, for example when the carboxy group participating in the reaction is in the form of an anhydride, may also be an acid-binding agent, with cooling or heating, for example in a temperature range from approximately −30° C. to approximately +150° C., especially approximately from 0° C. to +100° C., preferably from room temperature (approx. +20° C.) to +70° C., in an open or closed reaction vessel and/or in the atmosphere of an inert gas, for example nitrogen. Customary condensation agents are, for example, carbodiimides, for example N,N'-diethyl-, N,N'-dipropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium 3'-sulfonate and 2-tert-butyl-5-methyl-isoxazolium perchlorate, or a suitable acylamino compound, for example 2-ethoxy-1-ethoxycarbonyl-1,2-dihydroquinoline. Customary acid-binding condensation agents are, for example, alkali metal carbonates or hydrogen carbonates, for example sodium or potassium carbonate or hydrogen carbonate (customarily together with a sulfate), or organic bases, such as, customarily, pyridine or triethylamine, or sterically hindered tri-lower alkylamines, for example N,N-diisopropyl-N-ethylamine.

In a preferred variant, the carboxylic acid of formula II is reacted with an amine of formula III in a suitable solvent, such as e.g. N,N-dimethylformamide, in the presence of propylphosphonic anhydride or diethylcyanophosphanate and triethylamine, between 1 and 48 hours at between 0° C. and around 50° C., preferably at room temperature.

Protecting Groups

If one or more other functional groups, for example carboxy, hydroxy, amino, or mercapto, are or need to be protected in a compound of formula III, because they should not take part in the reaction, these are such groups as are usually used in the synthesis of amides, in particular peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis as cited hereinbefore, and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, "Protective Groups in Organic Synthesis", Wiley, New York.

Additional Process Steps

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

A compound of the formula I wherein $R_1$ is hydrogen can be converted to the respective compound wherein $R_1$ is lower alkyl by reaction e.g. with a diazo lower alkyl compound, especially diazomethane, in an inert solvent, preferably in the presence of a noble metal catalyst, especially in dispersed form, e.g. copper, or a noble metal salt, e.g. copper(I)-chloride or copper(II)-sulfate. Also reaction with lower alkylhalogenides is possible, or with other leaving group carrying lower alkanes, e.g. lower alkyl alcohols esterified by a strong organic sulfonic acid, such as a lower alkanesulfonic acid (optionally substituted by halogen, such as fluoro), an aromatic sulfonic acid, for example unsubstituted or substituted benzenesulfonic acid, the substituents preferably being selected from lower alkyl, such as methyl, halogen, such as bromo, and/or nitro, e.g. esterified by methanesulfonic acid, or p-toluene sulfonic acid. The alkylation takes place under usual conditions for alkylation of amides, especially in aqueous solution and/or in the presence of polar solvents, typically alcohols, for example methanol, ethanol, isopropanol, or ethylene glycol, or dipolar aprotic solvents, e.g. tetrahydrofuran, dioxane, or dimethylformamide, where applicable in the presence of acidic or basic catalysts, generally at temperatures from about 0° C. to the boiling temperature of the corresponding reaction mixture, preferably between 20° C. and reflux temperature, if necessary under increased pressure, e.g. in a sealed tube, and/or under inert gas, typically nitrogen or argon.

It should be emphasized that reactions analogous to the conversions mentioned in this chapter may also take place at the level of appropriate intermediates.

General Process Conditions

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the $H^+$ form, depending on the type of reaction and/or reactants at reduced, normal, or elevated temperature, for example in the range from –100° C. to about 190° C., preferably from about –80° C. to about 150° C., for example at –80 to –60° C., at room temperature, at –20 to 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula I is prepared according to or in analogy to the processes and process steps defined in the Examples.

The compounds of formula I, including their salts, are also obtainable in the form of hydrates, or their crystals can include for example the solvent used for crystallization (present as solvates).

Pharmaceutical Preparations, Methods, and Uses

The present invention relates furthermore to a method for the treatment of a neoplastic disease which responds to an inhibition of a protein kinase activity, which comprises administering a compound of formula I or a N-oxide or a pharmaceutically acceptable salt thereof, wherein the radicals and symbols have the meanings as defined above for formula I, in a quantity effective against said disease, to a warm-blooded animal requiring such treatment.

In particular the invention relates to a method for the treatment of leukaemia which responds to an inhibition of the Abl tyrosine kinase activity, which comprises administering a compound of formula I or a N-oxide or a pharmaceutically acceptable salt thereof, wherein the radicals and symbols have the meanings as defined above for formula I, in a quantity effective against said leukaemia, to a warm-blooded animal requiring such treatment.

The present invention relates also to pharmaceutical compositions that comprise a compound of formula I or a N-oxide thereof as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of formula I, a tautomer, a N-oxide or a pharmaceutically acceptable salt, or a hydrate or solvate thereof, and at least one pharmaceutically acceptable carrier.

The invention relates also to pharmaceutical compositions for use in a method for the pro-phylactic or especially therapeutic management of the human or animal body, to a process for the preparation thereof (especially in the form of compositions for the treatment of tumors) and to a method of treating tumor diseases, especially those mentioned hereinabove.

The invention relates also to processes and to the use of compounds of formula I or N-oxides thereof for the preparation of pharmaceutical preparations which comprise compounds of formula I or N-oxides thereof as active component (active ingredient).

In the preferred embodiment, a pharmaceutical preparation is suitable for administration to a warm-blooded animal, especially humans or commercially useful mammals suffering from a disease responsive to an inhibition of the Abl tyrosine kinase, for example chronic myelogenous leukaemia (CML), and comprises an effective quantity of a compound of formula I or N-oxides thereof for the inhibition of the Bcr-Abl fusion protein, or a pharmaceutically acceptable salt thereof, if salt-forming groups are present, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against the said diseases a novel compound of formula I or N-oxides thereof, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, sprays, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents or solubilizers.

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22 carbon atoms. The alcohol component of these fatty acid esters has a maximum of 6 carbon atoms and is a monovalent or polyvalent, for example a mono-, di- or trivalent, alcohol, especially glycol and glycerol.

Pharmaceutical compositions for oral administration can be obtained; for example, by combining the active ingredient with one or more solid carriers, if desired granulating a resulting mixture, and processing the mixture or granules, if desired or necessary, by the inclusion of additional excipients, to form tablets or tablet cores.

Suitable carriers are especially fillers, such as sugars, cellulose preparations, and/or calcium phosphates, and also binders, such as starches, and/or polyvinylpyrrolidone, and/or, if desired, disintegrators. Additional excipients are especially flow conditioners and lubricants.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations.

Pharmaceutical compositions for oral administration also include hard capsules consisting of gelatin, and also soft, sealed capsules consisting of gelatin and a plasticizer. The hard capsules may contain the active ingredient in the form of granules, for example in admixture with fillers, binders, and/or glidants, and optionally stabilizers. In soft capsules, the active ingredient is preferably dissolved or suspended in suitable liquid excipients, to which stabilizers and detergents may also be added.

Pharmaceutical compositions suitable for rectal administration are, for example, suppositories that consist of a combination of the active ingredient and a suppository base.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The invention relates likewise to a process or a method for the treatment of one of the pathological conditions mentioned hereinabove, especially a disease which responds to an inhibition of a tyrosine kinase, especially a corresponding neoplastic disease. The compounds of formula I or N-oxides thereof can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

The present invention relates especially also to the use of a compound of formula I or N-oxides thereof, or a pharmaceutically acceptable salt thereof, especially a compound of formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of a protein kinase, especially a neoplastic disease, more especially leukaemia which responds to an inhibition of the Abl tyrosine kinase.

The preferred dose quantity, composition, and preparation of pharmaceutical formulations (medicines) which are to be used in each case are described above.

Starting Materials

New starting materials and/or intermediates, as well as processes for the preparation thereof, are likewise the subject of this invention. In the preferred embodiment, such starting materials are used and reaction conditions so selected as to enable the preferred compounds to be obtained.

The substituted aminobenzoic acid of formula II, for example, can be obtained by reaction of an ester of 3-amino-4-$R_4$-benzoic acid, e.g. 3-amino-4-methylbenzoic acid, with cyanamide and condensing the obtainable guanidine with 3-(dimethylamino)-1-(3-pyridinyl)-2-propen-1-one, and finally hyrolysing the ester function.

Starting materials of the formula III are known, commercially available, or can be synthesized in analogy to or according to methods that are known in the art.

The following Examples serve to illustrate the invention without limiting the invention in its scope.

| Abbreviations | |
|---|---|
| DMSO | dimethylsulfoxide |
| HPLC/MS-MS | high-pressure liquid chromatography/tandem mass spectrometry |
| min | minutes |
| m.p. | melting point |
| NMP | N-methyl-pyrrolidone |
| NMR | nuclear magnetic resonance |
| PEG | polyethylen glycol |
| THF | tetrahydrofuran |

EXAMPLES

Example 1

N-(2-Furanylmethyl)-4-methyl-3-[[4-(3-pyridinyl)-2-pyrimidinyl]amino]benzamide

A solution containing ~50% of propylphosphonic anhydride in N,N-dimethylformamide (Fluka, Buchs, Switzerland; 674 µL, ~1 mmol) is added within 20 minutes to a stirred mixture of 4-methyl-3-[[4-(3-pyridinyl)-2-pyrimidinyl]amino]-benzoic acid (214.4 mg, 0.7 mmol), furfurylamine (Aldrich, Buchs, Switzerland; 61.8 µL, 0.7 mmol) and triethylamine (776 µL, 5.6 mmol) in 2 mL N,N-dimethylformamide. After stirring for 24 hours at room temperature, the mixture is treated with a half-saturated aqueous solution of sodium hydrogen carbonate and extracted three times with ethyl acetate. The solvent is evaporated off under reduced pressure and the residue dried in vacuo. The crude product is crystallised from dichloromethane to give the title compound as a crystalline solid.

$^1$H-NMR (400 MHz, DMSO-d$_6$, δ): 2.28 (s, 3H); 4.43 (d, 2H); 6.23 (m, 1H); 6.33-6.37 (m, 1H); 7.30 (d, 1H); 7.42 (d, 1H); 7.49 (ddd, 1H); 7.53 (m, 1H); 7.59 (dd, 1H); 8.11 (d, 1H); 8.38 (m, 1H); 8.49 (d, 1H); 8.66 (dd, 1H); 8.87 (t, 1H); 9.05 (s, 1H); 9.22 (m, 1H).

The starting material is prepared as follows:

Example 1a

3-[(Aminoiminomethyl)amino]-4-methyl-benzoic acid ethyl ester mononitrate

Cyanamide (Fluka, Buchs, Switzerland; 77.4 g, 1.842 mol) is added to a solution of 3-amino-4-methylbenzoic acid ethyl ester (J. Med. Chem. 16, 118-122, 1973; 150 g, 0.837 mol) in 850 mL of ethanol. Hydrochloric acid (Fluka, Buchs, Switzerland; 108 mL of 12M, 1.27 mol) is then added dropwise over 15 min and the reaction mixture is then stirred at 90° C. (bath temperature) for 15 hours. The solvent is evaporated off under reduced pressure to give a residue which is treated with water (1000 mL) and stirred with cooling at 5-10° C. A solution of ammonium nitrate (Merck, Darmstadt, Germany; 134.8 g, 1.68 mol) in water (400 mL) is added dropwise over 30 min. followed by ice-water (1200 mL). After stirring for an additional 30 min. the product is filtered off, washed with ice-water (3×1000 mL) and air-dried. The residue is washed with diethyl ether (2×2000 m L) and dried in vacuo at 500 to give the title compound as a crystalline solid, m.p. 195-197° C.

Example 1b

4-Methyl-3-[[4-(3-pyridinyl)-2-pyrimidinyl]amino]-benzoic acid ethyl ester

A stirred mixture of the intermediate Example 1a (164 g, 0.577 mol), 3-(dimethylamino)-1-(3-pyridinyl)-2-propen-1-one (113.8 g, 0.646 mol) and powdered NaOH (99%; Merck, Darmstadt, Germany; 26.6 g, 0.658 mol) in ethanol (2200 mL) is heated under reflux for 68 h. The reaction solvent is evaporated off under reduced pressure and the residue partitioned between ethyl acetate and water. The organic layer is separated and the aqueous phase extracted twice with ethyl acetate. The combined organic extracts are washed with water and brine, dried (Na$_2$SO$_4$) and the solvent is evaporated off under reduced pressure to give a residue, which is crystallised from diethyl ether to give the title compound as a crystalline solid, m.p. 95-96° C.

Example 1c

4-Methyl-3-[[4-(3-pyridinyl)-2-pyrimidinyl]amino]-benzoic acid

Aqueous sodium hydroxide (500 mL of 2M) is added dropwise to a stirred suspension of the intermediate Example 1b (132.8 g, 0.397 mol) in ethanol (1200 m L) and water (1200 mL). The reaction mixture is stirred at 45° C. for 2.5 h and then treated dropwise with aqueous HCl (1000 mL of 1M) over 1.5 hours. After addition of water (1000 mL) the precipitate is filtered off, washed with water (4×500 mL) and dried at room temperature. Residual water present in the air-dried product is removed by azeotropic distillation with toluene under reduced pressure. The dried toluene suspension is diluted with diethyl ether and filtered. The solid residue is washed with diethyl ether and dried in vacuo at 80° C. to give the title compound, m.p. 277-278° C.

Example 2

N-[4-Methyl-3-[[4-(3-pyridinyl)-2-pyrimidinyl]amino]benzoyl]-4-[(4-methyl-1-piperazinyl)methyl]benzeneamine A solution containing ~50% of propylphosphonic anhydride in N,N-dimethylformamide (Fluka, Buchs, Switzerland; 875 µL, ~1.5 mmol) is added within 20 minutes to a stirred mixture of 4-methyl-3-[[4-(3-pyridinyl)-2-pyrimidinyl]amino]-benzoic acid (306 mg, 1.0 mmol), 4-[(4-methyl-1-piperazinyl)methyl]benzeneamine (Chem. Abstr. Reg. Number: 70261-82-4; 205 mg, 1.0 mmol) and triethylamine (830 µL, 6.0 mmol) in 8 mL N,N-dimethylformamide. After stirring for 24 hours at room temperature, the mixture is treated with a saturated aqueous ammonium chloride and extracted three times with ethyl acetate. The solvent is evaporated off under reduced pressure and the residue dried in vacuo. The crude product is crystallised from ethanol-ethyl acetate to give the title compound as a crystalline solid, m.p. 153-155° C.

Example 3

1-[4-Methyl-3-[[4-(3-pyridinyl)-2-pyrimidinyl]amino]benzoyl]-4-(2-pyridinyl)-piperazine A solution containing ~50% of propylphosphonic anhydride in N,N-dimethylformamide (Fluka, Buchs, Switzerland; 674 µL, ~1 mmol) is added within 20 minutes to a stirred mixture of 4-methyl-3-[[4-(3-pyridinyl)-2-pyrimidinyl]amino]-benzoic acid (214.4 mg, 0.7 mmol), 1-(2-pyridyl)piperazine (Aldrich, Buchs, Switzerland; 114.3 mg, 0.7 mmol) and triethylamine (776 µL, 5.6 mmol) in 2 mL N,N-dimethylformamide. After stirring for 24 hours at room temperature, the mixture is treated with a half-saturated aqueous solution of sodium hydrogen carbonate and extracted three times with ethyl acetate. The solvent is evaporated off under reduced pressure and the residue dried in vacuo. The crude product is purified by column chromatography on silica gel, eluent 5-10% methanol in dichloromethane, to give the title compound as a solid. $^1$H-NMR (400 MHz, DMSO-d$_6$, δ): 2.31 (s, 3H); 3.35-3.74 (m, 8H); 6.65 (ddd, 1H); 6.79 (d, 1H); 7.13 (dd, 1H); 7.32 (d, 1H); 7.44 (d, 1H); 7.49-7.56 (m, 2H);

7.69 (m, 1H); 8.11 (m, 1H); 8.40 (m, 1H); 8.52 (d, 1H); 8.66 (dd, 1H); 9.06 (s, 1H); 9.24 (m, 1H).

The following compounds are prepared analogously by utilising the appropriate amine (supplier in parenthesis):

Example 4

4-Methyl-N-[2-(2-pyridinyl)ethyl]-3-[[4-(3-pyridinyl)-2-pyrimidinyl]amino]-benzamide utilising 2-(2-aminoethyl)pyridine (Fluka, Buchs, Switzerland)

$^1$H-NMR (400 MHz, DMSO-d$_6$, δ): 2.27 (s, 3H); 2.97 (t, 2H); 3.58 (m, 2H); 7.18 (ddd, 1H); 7.25 (m, 1H); 7.29 (d, 1H); 7.42 (d, 1H); 7.47-7.56 (m, 2H); 7.65 (m, 1H); 8.06 (d, 1H); 8.39 (m, 1H); 8.44-8.51 (m, 3H); 8.66 (dd, 1H); 9.04 (s, 1H); 9.22 (m, 1H).

Example 5

4-Methyl-N-[1-(phenylmethyl)-4-piperidinyl]-3-[[4-(3-pyridinyl)-2-pyrimidinyl]-amino]benzamide utilising 4-amino-1-benzylpiperidine (Aldrich, Buchs, Switzerland)

$^1$H-NMR (400 MHz, DMSO-d$_6$, δ): 1.47-1.63 (m, 2H); 1.69-1.80 (m, 2H); 1.92-2.05 (m, 2H); 2.27 (s, 3H); 2.73-2.83 (m, 2H); 3.43 (s, 2H); 3.68-3.83 (m, 1H); 7.18-7.33 (m, 6H); 7.42 (d, 1H); 7.49 (ddd, 1H); 7.55 (dd, 1H); 8.10 (m, 1H); 8.14 (d, 1H); 8.37 (m, 1H); 8.49 (d, 1H); 8.65 (dd, 1H); 9.04 (s, 1H); 9.21 (m, 1H).

Example 6

4-Methyl-N-(4-pyridinylmethyl)-3-[[4-(3-pyridinyl)-2-pyrimidinyl]amino]benzamide utilising 4-(aminomethyl)pyridine (Aldrich, Buchs, Switzerland)

$^1$H-NMR (400 MHz, DMSO-d$_6$, δ): 2.30 (s, 3H); 4.46 (d, 2H); 7.26 (m, 2H); 7.33 (d, 1H); 7.43 (d, 1H); 7.47 (ddd, 1H); 7.62 (dd, 1H); 8.16 (d, 1H); 8.38 (m, 1H); 8.45 (m, 2H); 8.50 (d, 1H); 8.66 (dd, 1H); 9.03 (t, 1H); 9.08 (s, 1H); 9.23 (m, 1H).

Example 7

4-Methyl-N-[2-(1-methyl-1H-pyrrol-2-yl)ethyl]-3-[[4-(3-pyridinyl)-2-pyrimidinyl]-amino]benzamide utilising 2-(2-aminoethyl)-1-methylpyrrol [Chem. Abstr. Reg. Number: 83732-75-6]

$^1$H-NMR (400 MHz, DMSO-d$_6$, δ): 2.28 (s, 3H); 2.75 (t, 2H); 3.42 (m, 2H); 3.51 s, 3H); 5.76-5.85 (m, 2H); 6.57 (m, 1H); 7.30 (d, 1H); 7.43 (d, 1H); 7.46-7.58 (m, 2H); 8.10 (br. 1H); 8.40 (m, 1H); 8.48-8.55 (m, 2H); 8.64-8.69 (m, 1H); 9.05 (s, 1H); 9.23 (m, 1H).

Example 8

N-[(4-Methoxyphenyl)methyl]-4-methyl-3-[[4-(3-pyridinyl)-2-pyrimidinyl]amino]-benzamide utilising 4-methoxybenzylamine (Fluka, Buchs, Switzerland)

$^1$H-NMR (400 MHz, DMSO-d$_6$, δ): 2.28 (s, 3H); 3.69 (s, 3H); 4.37 (d, 2H); 6.80-6.87 (m, 2H); 7.17-7.23 (m, 2H); 7.31 (d, 1H); 7.42 (d, 1H); 7.47 (ddd, 1H); 7.59 (dd, 1H); 8.11 (d, 1H); 8.38 (m, 1H); 8.49 (d, 1H); 8.66 (dd, 1H); 8.87 (t, 1H); 9.05 (s, 1H); 9.23 (m, 1H).

Example 9

4-Methyl-N-(2-methylpropyl)-3-[[4-(3-pyridinyl)-2-pyrimidinyl]amino]benzamide utilising isobutylamine (Fluka, Buchs, Switzerland)

$^1$H-NMR (400 MHz, DMSO-d$_6$, δ): 0.85 (d, 6H); 1.81 (m, 1H); 2.27 (s, 3H); 3.04 (m, 2H); 7.29 (d, 1H); 7.42 (d, 1H); 7.48 (dd, 1H); 7.55 (dd, 1H); 8.07 (d, 1H); 8.31-8.41 (m, 2H); 8.49 (d, 1H); 8.65 (dd, 1H); 9.05 (s, 1H); 9.22 (m, 1H).

Example 10

4-Methyl-N-(2-morpholinoethyl)-3-[[4-(3-pyridinyl)-2-pyrimidinyl]amino]-benzamide utilising 4-(2-aminoethyl)morpholine (Fluka, Buchs, Switzerland)

$^1$H-NMR (400 MHz, DMSO-d$_6$, δ): 2.28 (s, 3H); 2.33-2.46 (m, 6H); 3.30-3.40 (m, 2H); 3.53 (m, 4H); 7.30 (d, 1H); 7.42 (d, 1H); 7.46-7.57 (m, 2H); 8.06 (d, 1H); 8.30 (m, 1H); 8.38 (m, 1H); 8.49 (d, 1H); 8.66 (dd, 1H); 9.05 (s, 1H); 9.22 (m, 1H).

Example 11

4-Methyl-3-[[4-(3-pyridinyl)-2-pyrimidinyl]amino]-1-[(tetrahydro-2-furanyl)-methyl]benzamide utilising tetrahydrofurfurylamine (Fluka, Buchs, Switzerland)

$^1$H-NMR (400 MHz, DMSO-d$_6$, δ): 1.49-1.63 (m, 1H); 1.70-1.93 (m, 3H); 2.27 (s, 3H); 3.27 (m, 2H); 3.58 (m, 1H); 3.72 (m, 1H); 3.94 (m, 1H); 7.29 (d, 1H); 7.42 (d, 1H); 7.49 (ddd, 1H); 7.56 (dd, 1H); 8.08 (d, 1H); 8.35-8.45 (m, 2H); 8.49 (d, 1H); 8.66 (dd, 1H); 9.04 (s, 1H); 9.21 (m, 1H).

Example 12

N-[2-(2,4-Dihydroxy-5-pyrimidinyl)ethyl]-4-methyl-3-[[4-(3-pyridinyl)-2-pyrimidinyl]amino]benzamide utilising 5-(2-aminoethyl)-2,4(1H,3H)-pyrimidinedione [Chem. Abstr. Reg. Number: 221170-25-8]

$^1$H-NMR (400 MHz, DMSO-d$_6$, δ): 2.27 (s, 3H); 2.40 (t, 2H); 3.34 (m, 2H); 7.15 (m, 1H); 7.29 (d, 1H); 7.42 (d, 1H); 7.47-7.55 (m, 2H); 8.07 (d, 1H); 8.35-8.42 (m, 2H); 8.49 (d, 1H); 8.66 (dd, 1H); 9.04 (s, 1H); 9.22 (m, 1H); 10.59 (s, 1H); 11.01 (s, 1H).

Example 13

N-Cyclohexyl-4-methyl-3-[[4-(3-pyridinyl)-2-pyrimidinyl]amino]benzamide utilising cyclohexylamine (Fluka, Buchs, Switzerland)

$^1$H-NMR (400 MHz, DMSO-d$_6$, δ): 1.00-1.16 (m, 1H); 1.18-1.36 (m, 4H); 1.52-1.85 (m, 5H); 2.27 (s, 3H); 3.66-3.82 (m, 1H); 7.28 (d, 1H); 7.41 (d, 1H); 7.48 (m, 1H); 7.55 (dd, 1H); 8.06-8.12 (m, 2H); 8.37 (m, 1H); 8.49 (d, 1H); 8.66 (dd, 1H); 9.04 (s, 1H); 9.21 (m, 1H).

Example 14

N-[(3S)—Hexahydro-2-oxo-1H-azepin-3-yl]-4-methyl-3-[[4-(3-pyridinyl)-2-pyrimidinyl]amino]benzamide utilising L(−)-alpha-amino-epsilon-caprolactam [Chem. Abstr. Reg. Number: 21568-87-6]

$^1$H-NMR (400 MHz, DMSO-d$_6$, δ): 1.11-1.31 (m, 1H); 1.37-1.82 (m, 3H); 1.83-1.96 (m, 2H); 2.28 (s, 3H); 3.00-3.13 (m, 1H); 3.15-3.30 (m, 1H); 4.58 (m, 1H); 7.32 (d, 1H); 7.43 (d, 1H); 7.51 (ddd, 1H); 7.55 (dd, 1H); 7.84 (m, 1H); 8.08 (d, 1H); 8.13 (d, 1H); 8.40 (m, 1H); 8.50 (d, 1H); 8.66 (dd, 1H); 9.06 (s, 1H); 9.22 (m, 1H).

Example 15

N-[2-(3,4-Dimethoxyphenyl)ethyl]-4-methyl-3-[[4-(3-pyridinyl)-2-pyrimidinyl]-amino]benzamide utilising 2-(3,4-dimethoxyphenyl)ethylamine (Fluka, Buchs, Switzerland)

$^1$H-NMR (400 MHz, DMSO-d$_6$, δ): 2.27 (s, 3H); 2.75 (t, 2H); 3.43 (m, 2H); 3.67 (s, 6H); 6.70 (dd, 1H); 6.77-6.83 (m, 2H); 7.30 (d, 1H); 7.42 (d, 1H); 7.46-7.57 (m, 2H); 8.07 (d, 1H); 8.36-8.46 (m, 2H); 8.49 (d, 1H); 8.66 (dd, 1H); 9.05 (s, 1H); 9.22 (m, 1H).

Example 16

2-[[4-Methyl-3-[[4-(3-pyridinyl)-2-pyrimidinyl]amino]benzoyl]amino]-4-thiazole-acetic acid ethyl ester utilising ethyl 2-amino-4-thiazoleacetate (Aldrich, Buchs, Switzerland)

$^1$H-NMR (400 MHz, DMSO-d$_6$, δ): 1.16 (t, 3H); 2.32 (s, 3H); 3.70 (s, 2H); 4.06 (q, 2H); 7.01 (s, 1H); 7.36 (d, 1H); 7.42-7.54 (m, 2H); 7.82 (d, 1H); 8.34-8.47 (m, 2H); 8.52 (d, 1H); 8.66 (m, 1H); 9.08 (s, 1H); 9.24 (m, 1H); 12.57 (br., 1H).

Example 17

N-[3-(1H-Imidazol-1-yl)propyl]-4-methyl-3-[[4-(3-pyridinyl)-2pyrimidinyl]amino]-benzamide utilising 1-(3-aminopropyl)imidazole (Aldrich, Buchs, Switzerland)

$^1$H-NMR (400 MHz, DMSO-d$_6$, δ): 1.96 (qui, 2H); 2.30 (s, 3H); 3.24 (m, 2H); 4.01 (t, 2H); 6.91 (s, 1H); 7.22 (m, 1H); 7.34 (d, 1H); 7.45 (d, 1H); 7.51 (ddd, 1H); 7.59 (dd, 1H); 7.70 (s, 1H); 8.14 (d, 1H); 8.42 (m, 1H); 8.47 (t, 1H); 8.52 (d, 1H); 8.68 (dd, 1H); 9.10 (s, 1H); 9.25 (m, 1H).

Example 18

N-(Cyclopropylmethyl)-4-methyl-3-[[4-(3-pyridinyl)-2-pyrimidinyl]amino]-benzamide utilising cyclopropanemethylamine (Fluka, Buchs, Switzerland)

$^1$H-NMR (400 MHz, DMSO-d$_6$, δ): 0.17-0.22 (m, 2H); 0.36-0.42 (m, 2H); 0.96-1.06 (m, 1H); 2.28 (s, 3H); 3.11 (m, 2H); 7.31 (d, 1H); 7.43 (d, 1H); 7.50 (ddd, 1H); 7.58 (dd, 1H); 8.10 (d, 1H); 8.40 (m, 1H); 8.47 (t, 1H); 8.50 (d, 1H); 8.67 (dd, 1H); 9.07 (s, 1H); 9.23 (m, 1H).

Example 19

N-(2-methoxyethyl)-4-methyl-3-[[4-(3-pyridinyl)-2-pyrimidinyl]amino]benzamide utilising 2-methoxyethylamine (Fluka, Buchs, Switzerland)

$^1$H-NMR (400 MHz, DMSO-d$_6$, δ): 2.28 (s, 3H); 3.23 (s, 3H); 3.36-3.46 (m, 4H); 7.31 (d, 1H); 7.43 (d, 1H); 7.51 (ddd, 1H); 7.57 (dd, 1H); 8.10 (d, 1H); 8.38-8.47 (m, 2H); 8.50 (d, 1H); 8.68 (dd, 1H); 9.07 (s, 1H); 9.23 (m, 1H).

Example 20

4-Methyl-N-[3-(2-oxo-1-pyrrolidinyl)propyl]-3-[[4-(3-pyridinyl)-2-pyrimidinyl]-amino]benzamide utilising 1-(3-aminopropyl)-2-pyrrolidinone (Aldrich, Buchs, Switzerland)

$^1$H-NMR (400 MHz, DMSO-d$_6$, δ): 1.67 (m, 2H); 1.89 (m, 2H); 2.18 (t, 2H); 2.28 (s, 3H); 3.19 (m, 4H); 3.32 (m, 2H); 7.30 (d, 1H); 7.42 (d, 1H); 7.49 (ddd, 1H); 7.54 (dd, 1H); 8.09 (d, 1H); 8.31-8.42 (m, 2H); 8.49 (d, 1H); 8.66 (dd, 1H); 9.04 (s, 1H); 9.22 (m, 1H).

Example 21

N,4-Dimethyl-N-(phenylmethyl)-3-[[4-(3-pyridinyl)-2-pyrimidinyl]amino]-benzamide utilising N-benzylmethylamine (Fluka, Buchs, Switzerland)

$^1$H-NMR (400 MHz, DMSO-d$_6$, δ): 2.28 (s, 3H); 2.86 (s, 3H); 4.51-4.68 (m, 2H); 7.08-7.35 (m, 7H); 7.43 (d, 1H); 7.48 (m, 1H); 7.71 (s, 1H); 8.35-8.54 (m, 2H); 8.67 (m, 1H); 8.97-9.09 (m, 1H); 9.24 (m, 1H).

Example 22

N-[4-(Acetylamino)phenyl]-4-methyl-3-[[4-(3-pyridinyl)-2-pyrimidinyl]amino]-benzamide utilising 4-aminoacetanilide (Fluka, Buchs, Switzerland)

$^1$H-NMR (400 MHz, DMSO-d$_6$, δ): 2.01 (s, 3H); 2.32 (s, 3H); 7.38 (d, 1H); 7.45 (d, 1H); 7.47-7.54 (m, 3H); 7.63-7.71 (m, 3H); 8.22 (m, 1H); 8.43 (m, 1H); 8.52 (d, 1H); 8.67 (dd, 1H); 9.13 (s, 1H); 9.25 (m, 1H); 9.90 (s, 1H); 10.11 (s, 1H).

Example 23

N-(4-Methoxy-2-methylphenyl)-4-methyl-3-[[4-(3-pyridinyl)-2-pyrimidinyl]amino]-benzamide utilising 4-methoxy-2-methylaniline (Aldrich, Buchs, Switzerland)

$^1$H-NMR (400 MHz, DMSO-d$_6$, δ): 2.16 (s, 3H); 2.32 (s, 3H); 3.73 (s, 3H); 6.75 (dd, 1H); 6.82 (m, 1H); 7.16 (d, 1H); 7.37 (d, 1H); 7.45 (d, 1H); 7.49 (ddd, 1H); 7.69 (dd, 1H); 8.25 (d, 1H); 8.41 (m, 1H); 8.52 (d, 1H); 8.67 (dd, 1H); 9.12 (s, 1H); 9.25 (m, 1H); 9.69 (s, 1H).

Example 24

4-Methyl-N-[4-(methylsulfonyl)benzyl]-3-[[4-(3-pyridinyl)-2-pyrimidinyl]amino]-benzamide utilising 4-methylsulfonylbenzylamine hydrochloride (Acros, Morris Plains, N.J.)

$^1$H-NMR (400 MHz, DMSO-$d_6$, δ): 2.30 (s, 3H); 3.16 (s, 3H); 4.54 (d, 2H); 7.34 (d, 1H); 7.44 (d, 1H); 7.49 (ddd, 1H); 7.55 (m, 2H); 7.63 (dd, 1H); 7.86 (m, 2H); 8.16 (d, 1H); 8.40 (m, 1H); 8.51 (d, 1H); 8.67 (dd, 1H); 9.10 (m, 2H); 9.24 (m, 1H).

Example 25

N-[[4-(Dimethylamino)phenyl]methyl]-4-methyl-3-[[4-(3-pyridinyl)-2-pyrimidinyl]-amino]benzamide utilising 4-(dimethylamino)benzylamine dihydrochloride (Aldrich, Buchs, Switzerland)

$^1$H-NMR (400 MHz, DMSO-$d_6$, δ): 2.28 (s, 3H); 2.82 (s, 6H); 4.32 (d, 2H); 6.64 (m, 2H); 7.11 (m, 2H); 7.31 (d, 1H); 7.43 (d, 1H); 7.48 (ddd, 1H); 7.59 (dd, 1H); 8.12 (d, 1H); 8.39 (m, 1H); 8.50 (d, 1H); 8.68 (dd, 1H); 8.81 (t, 1H); 9.07 (s, 1H); 9.24 (m, 1H).

Example 26

N-(2-Amino-2-oxoethyl)-4-methyl-3-[[4-(3-pyridinyl)-2-pyrimidinyl]amino]-benzamide utilising glycinamide hydrochloride (Fluka, Buchs, Switzerland)

$^1$H-NMR (400 MHz, DMSO-$d_6$, δ): 2.29 (s, 3H); 3.78 (d, 2H); 7.02 (s, 1H); 7.30-7.36 (m, 2H); 7.44 (d, 1H); 7.53 (ddd, 1H); 7.61 (dd, 1H); 8.11 (m, 1H); 8.41 (m, 1H); 8.50 (d, 1H); 8.57 (t, 1H); 8.67 (dd, 1H); 9.08 (s, 1H); 9.24 (m, 1H).

Example 27

N-[4-Methyl-3-[[4-(3-pyridinyl)-2-pyrimidinyl]amino]benzoyl]glycine methyl ester utilising glycine methylester hydrochloride (Fluka, Buchs, Switzerland)

$^1$H-NMR (400 MHz, DMSO-$d_6$, δ): 2.29 (s, 3H); 3.63 (s, 3H); 3.98 (d, 2H); 7.34 (d, 1H); 7.44 (d, 1H); 7.52 (ddd, 1H); 7.59 (dd, 1H); 8.11 (d, 1H); 8.41 (m, 1H); 8.50 (d, 1H); 8.67 (dd, 1H); 8.87 (t, 1H); 9.09 (s, 1H); 9.23 (m, 1H).

Example 28

N-[4-Methyl-3-[[4-(3-pyridinyl)-2-pyrimidinyl]amino]benzoyl]beta-alanine methyl ester utilising beta-alanine methylester hydrochloride (Fluka, Buchs, Switzerland)

$^1$H-NMR (400 MHz, DMSO-$d_6$, δ): 2.27 (s, 3H); 2.57 (t, 2H); 3.46 (m, 2H); 3.57 (s, 3H); 7.31 (d, 1H); 7.43 (d, 1H); 7.50-7.55 (m, 2H); 8.07 (d, 1H); 8.40 (m, 1H); 8.47 (t, 1H); 8.50 (d, 1H); 8.67 (dd, 1H); 9.07 (s, 1H); 9.23 (m, 1H).

Example 29

N-[[4-(Aminosulfonyl)phenyl]methyl]-4-methyl-3-[[4-(3-pyridinyl)-2-pyrimidinyl]-amino]benzamide utilising p-(aminomethyl)benzenesulfonamide hydrochloride (Sigma, Buchs, Switzerland)

$^1$H-NMR (400 MHz, DMSO-$d_6$, δ): 2.29 (s, 3H); 4.51 (d, 2H); 7.30 (s, 2H); 7.34 (d, 1H); 7.43-7.50 (m, 4H); 7.62 (dd, 1H); 7.75 (m, 2H); 8.16 (d, 1H); 8.40 (m, 1H); 8.51 (d, 1H); 8.68 (dd, 1H); 9.06 (t, 1H); 9.09 (s, 1H); 9.24 (m, 1H).

Example 30

N-(3-Hydroxypropyl)-4-methyl-3-[[4-(3-pyridinyl)-2-pyrimidinyl]amino]benzamide utilising 3-amino-1-propanol (Aldrich, Buchs, Switzerland)

$^1$H-NMR (400 MHz, DMSO-$d_6$, δ): 1.65 (qui, 2H); 2.28 (s, 3H); 3.29 (m, 2H); 3.42 (m, 2H); 4.50 (m, 1H); 7.30 (d, 1H); 7.43 (d, 1H); 7.51 (ddd, 1H); 7.56 (dd, 1H); 8.09 (d, 1H); 8.36-8.43 (m, 2H); 8.50 (d, 1H); 8.67 (dd, 1H); 9.07 (s, 1H); 9.23 (m, 1H).

Example 31

N,N-Diethyl-4-methyl-3-[[4-(3-pyridinyl)-2-pyrimidinyl]amino]benzamide utilising diethylamine (Fluka, Buchs, Switzerland)

$^1$H-NMR (400 MHz, DMSO-$d_6$, δ): 1.04 (m, 6H); 2.28 (s, 3H); 3.31 (m, 4H); 7.02 (dd, 1H); 7.27 (d, 1H); 7.44 (d, 1H); 7.51 (ddd, 1H); 7.61 (m, 1H); 8.39 (m, 1H); 8.51 (d, 1H); 8.68 (dd, 1H); 9.01 (s, 1H); 9.23 (m, 1H).

Example 32

N-[4-Methyl-3-[[4-(3-pyridinyl)-2-pyrimidinyl]amino]benzoyl]-(L)-phenylalanine 1,1-dimethylethyl ester utilising L-phenylalanine t-butylester hydrochloride (Novabiochem (Juro), Lucerne, Switzerland)

$^1$H-NMR (400 MHz, DMSO-$d_6$, δ): 1.32 (s, 9H); 2.28 (s, 3H); 3.07 (m, 2H); 4.53 (m, 1H); 7.13-7.29 (m, 5H); 7.32 (d, 1H); 7.44 (d, 1H); 7.50 (ddd, 1H); 7.55 (dd, 1H); 8.05 (m, 1H); 8.39 (m, 1H); 8.49 (d, 1H); 8.63 (d, 1H); 8.67 (dd, 1H); 9.08 (s, 1H); 9.23 (m, 1H).

Example 33

N-[4-Methyl-3-[[4-(3-pyridinyl)-2-pyrimidinyl]amino]benzoyl]-(D)-alanine 1,1-dimethylethyl ester utilising D-alanine t-butylester hydrochloride (Novabiochem (Juro), Lucerne, Switzerland)

$^1$H-NMR (400 MHz, DMSO-$d_6$, δ): 1.34 (d, 3H); 1.38 (s, 9H); 2.28 (s, 3H); 4.32 (m, 1H); 7.33 (d, 1H); 7.43 (d, 1H); 7.51 (ddd, 1H); 7.61 (dd, 1H); 8.14 (m, 1H); 8.40 (m, 1H); 8.50 (m, 1H); 8.58 (d, 1H); 8.67 (dd, 1H); 9.08 (s, 1H); 9.23 (m, 1H).

Example 34

N-[1-[4-Methyl-3-[[4-(3-pyridinyl)-2-pyrimidinyl]amino]benzoyl]-4-piperidinyl]-benzamide utilising N-4-piperidinyl-benzamide (Maybridge Chemical Co. Ltd)

$^1$H-NMR (400 MHz, DMSO-d$_6$, δ): 1.49 (m, 2H); 1.68-1.94 (m, 2H); 2.30 (s, 3H); 2.92 (m, 1H); 3.16 (m, 1H); 3.79 (m, 1H); 4.05 (m, 1H); 4.42 (m, 1H); 7.08 (dd, 1H); 7.31 (d, 1H); 7.41-7.54 (m, 5H); 7.63 (m, 1H); 7.79-7.84 (m, 2H); 8.28 (d, 1H); 8.40 (m, 1H); 8.51 (d, 1H); 8.66 (dd, 1H); 9.06 (s, 1H); 9.24 (m, 1H).

Example 35

4-[4-Methyl-3-[[4-(3-pyridinyl)-2-pyrimidinyl]amino]benzoyl]-morpholine utilising morpholine (Fluka, Buchs, Switzerland)

$^1$H-NMR (400 MHz, DMSO-d$_6$, δ): 2.29 (s, 3H); 3.47 (m, 8H); 7.10 (dd, 1H); 7.30 (d, 1H); 7.44 (m, 1H); 7.52 (ddd, 1H); 7.65 (m, 1H); 8.40 (m, 1H); 8.51 (d, 1H); 8.69 (dd, 1H); 9.05 (s, 1H); 9.23 (m, 1H).

Example 36

1-(4-Methoxyphenyl)-4-[4-methyl-3-[[4-(3-pyridinyl)-2-pyrimidinyl]amino]-benzoyl]piperazine utilising 1-(4-methoxyphenyl)-piperazine (Emka Chemie, Neufahrn, Germany)

$^1$H-NMR (400 MHz, DMSO-d$_6$, δ): 2.30 (s, 3H); 2.87-3.08 (m, 4H); 3.50-3.75 (m, 4H); 3.67 (s, 3H); 6.78-6.88 (m, 4H); 7.12 (dd, 1H); 7.31 (d, 1H); 7.44 (m, 1H); 7.51 (ddd, 1H); 7.67 (m, 1H); 8.38 (m, 1H); 8.52 (m, 1H); 8.67 (dd, 1H); 9.06 (s, 1H); 9.23 (m, 1H).

Example 37

1-[4-Methyl-3-[[4-(3-pyridinyl)-2-pyrimidinyl]amino]benzoyl]-4-(4-pyridinyl)-piperazine utilising 1-(4-pyridyl)-piperazine (Emka Chemie, Neufahrn, Germany)

$^1$H-NMR (400 MHz, DMSO-d$_6$, δ): 2.31 (s, 3H); 3.30 (m, 4H); 3.59 (m, 4H); 6.77 (m, 2H); 7.14 (dd, 1H); 7.32 (d, 1H); 7.45 (d, 1H); 7.52 (ddd, 1H); 7.70 (m, 1H); 8.16 (m, 2H); 8.41 (m, 1H); 8.53 (d, 1H); 8.67 (dd, 1H); 9.07 (s, 1H); 9.24 (m, 1H).

Example 38

1-[4-Methyl-3-[[4-(3-pyridinyl)-2-pyrimidinyl]amino]benzoyl]-4-(pyrazinyl)-piperazine utilising 1-(2-pyrazinyl)-piperazine (Emka Chemie, Neufahrn, Germany)

$^1$H-NMR (400 MHz, DMSO-d$_6$, δ): 2.31 (s, 3H); 3.57 (m, 8H); 7.14 (dd, 1H); 7.32 (d, 1H); 7.45 (d, 1H); 7.51 (ddd, 1H); 7.72 (m, 1H); 7.85 (d, 1H); 8.08 (d, 1H); 8.29 (d, 1H); 8.40 (m, 1H); 8.53 (d, 1H); 8.65 (dd, 1H); 9.06 (s, 1H); 9.24 (m, 1H).

Example 39

1-[4-Methyl-3-[[4-(3-pyridinyl)-2-pyrimidinyl]amino]benzoyl]-4-(phenylmethyl)-piperazine utilising 1-benzyl-piperazine (Aldrich, Buchs, Switzerland)

$^1$H-NMR (400 MHz, DMSO-d$_6$, δ): 2.21-2.42 (m, 4H); 2.28 (s, 3H); 3.34-3.63 (m, 6H); 7.07 (dd, 1H); 7.21-7.34 (m, 6H); 7.43-7.50 (m, 2H); 7.63 (m, 1H); 8.38 (m, 1H); 8.50 (d, 1H); 8.65 (dd, 1H); 9.03 (s, 1H); 9.22 (m, 1H).

Example 40

1-Cyclopentyl-4-[4-methyl-3-[[4-(3-pyridinyl)-2-pyrimidinyl]amino]benzoyl]-piperazine utilising 1-cyclopentyl-piperazine (Emka Chemie, Neufahm, Germany)

$^1$H-NMR (400 MHz, DMSO-d$_6$, δ): 1.20-1.31 (m, 2H); 1.39-1.62 (m, 4H); 1.65-1.75 (m, 2H); 2.18-2.47 (m, 8H); 3.27-3.62 (m, 4H); 7.08 (dd, 1H); 7.29 (d, 1H); 7.44 (d, 1H); 7.51 (ddd, 1H); 7.62 (m, 1H); 8.38 (m, 1H); 8.51 (d, 1H); 8.68 (dd, 1H); 9.04 (s, 1H); 9.22 (m, 1H).

Example 41

4-{{4-[4-Methyl-3-[[4-(3-pyridinyl)-2-pyrimidinyl]amino]benzoyl]-1-piperazinyl}-acetyl}morpholine utilising 4-[2-(piperazin-1-yl)-acetyl]-morpholine (Emka Chemie, Neufahm, Germany)

$^1$H-NMR (400 MHz, DMSO-d$_6$, δ): 2.29 (s, 3H); 2.31-2.49 (m, 4H); 3.16 (s, 2H); 3.37-3.60 (m, 12H); 7.07 (dd, 1H); 7.29 (d, 1H); 7.45 (d, 1H); 7.52 (ddd, 1H); 7.65 (m, 1H); 8.39 (m, 1H); 8.51 (d, 1H); 8.68 (dd, 1H); 9.04 (s, 1H); 9.23 (m, 1H).

Example 42

1-[4-Methyl-3-[[4-(3-pyridinyl)-2-pyrimidinyl]amino]benzoyl]-4-[2-oxo-2-(1-pyrrolidinyl)ethyl]piperazine utilising 1-[2-(piperazin-1-yl)-acetyl-pyrrolidine (Emka Chemie, Neufahrn, Germany)

$^1$H-NMR (400 MHz, DMSO-d$_6$, δ): 1.73 (m, 2H); 1.83 (m, 2H); 2.29 (s, 3H); 2.43 (m, 4H); 3.09 (s, 2H); 3.25 (m, 2H); 3.34-3.63 (m, 6H); 7.07 (dd, 1H); 7.29 (d, 1H); 7.45 (d, 1H); 7.52 (ddd, 1H); 7.64 (m, 1H); 8.39 (m, 1H); 8.51 (d, 1H); 8.68 (dd, 1H); 9.04 (s, 1H); 9.22 (m, 1H).

Example 43

4-[4-Methyl-3-[[4-(3-pyridinyl)-2-pyrimidinyl]amino]benzoyl]-1-piperazine carboxylic acid ethyl ester utilising ethyl 1-piperazinecarboxylate (Aldrich, Buchs, Switzerland)

$^1$H-NMR (400 MHz, DMSO-d$_6$, δ): 1.16 (t, 3H); 2.29 (s, 3H); 3.19-3.63 (m, 8H); 4.02 (q, 2H); 7.10 (dd, 1H); 7.30 (d, 1H); 7.45 (d, 1H); 7.52 (ddd, 1H); 7.66 (m, 1H); 8.40 (m, 1H); 8.51 (d, 1H); 8.68 (dd, 1H); 9.06 (s, 1H); 9.23 (m, 1H).

Example 44

2-[4-Methyl-3-[[4-(3-pyridinyl)-2-pyrimidinyl]amino]benzoyl]-1,2,3,4-tetrahydro isoquinoline utilising 1,2,3,4-tetrahydroisoquinoline (Fluka, Buchs, Switzerland)

$^1$H-NMR (400 MHz, DMSO-$d_6$, δ): 2.31 (s, 3H); 2.79 (m, 2H); 3.57-3.90 (m, 2H); 4.58-4.79 (m, 2H); 7.08-7.23 (m, 5H); 7.32 (d, 1H); 7.42-7.50 (m, 2H); 7.70 (m, 1H); 8.39 (m, 1H); 8.51 (d, 1H); 8.67 (dd, 1H); 9.05 (s, 1H); 9.24 (m, 1H).

Example 45

N,N-bis(2-Methoxyethyl)-4-methyl-3-[[4-(3-pyridinyl)-2-pyrimidinyl]amino]-benzamide utilising bis(2-methoxyethyl)amine (Aldrich, Buchs, Switzerland)

$^1$H-NMR (400 MHz, DMSO-$d_6$, δ): 2.28 (s, 3H); 3.09 (br.s, 3H); 3.23 (br.s, 3H); 3.47 (m, 8H); 7.04 (dd, 1H); 7.27 (d, 1H); 7.44 (d, 1H); 7.51 (ddd, 1H); 7.62 (m, 1H); 8.39 (m, 1H); 8.51 (d, 1H); 8.68 (dd, 1H); 9.01 (s, 1H); 9.23 (m, 1H).

Example 46

1'-[4-Methyl-3-[[4-(3-pyridinyl)-2-pyrimidinyl]amino]benzoyl]-1,4'-bipiperidine utilising 4-piperidinopiperidine (Aldrich, Buchs, Switzerland)

$^1$H-NMR (400 MHz, DMSO-$d_6$, δ): 1.21-1.50 (m, 8H); 1.51-1.83 (m, 2H); 2.29 (s, 3H); 2.39 (m, 4H); 2.68 (m, 1H); 2.95 (m, 1H); 3.71 (m, 1H); 4.42 (m, 1H); 7.07 (dd, 1H); 7.28 (d, 1H); 7.45 (d, 1H); 7.52 (ddd, 1H); 7.63 (m, 1H); 8.40 (m, 1H); 8.51 (d, 1H); 8.67 (dd, 1H); 9.03 (s, 1H); 9.23 (m, 1H).

Example 47

N-[4-Methyl-3-[[4-(3-pyridinyl)-2-pyrimidinyl]amino]benzoyl]-N-(phenylmethyl)-glycine ethyl ester utilising N-benzylglycine ethyl ester (Fluka, Buchs, Switzerland)

$^1$H-NMR (300 MHz, DMSO-$d_6$, δ): 0.97-1.20 (m, 3H); 2.27 (s, 3H); 3.90-4.12 (m, 4H); 4.58-4.68 (m, 2H); 7.07 (m, 1H); 7.15-7.34 (m, 6H); 7.38-7.53 (m, 2H); 7.65-7.74 (m, 1H); 8.35-8.51 (m, 2H); 8.66 (dd, 1H); 8.96-9.04 (m, 1H); 9.22 (m, 1H).

Example 48

N-(3-Chlorophenyl)-4-methyl-3-[[4-(3-pyridinyl)-2-pyrimidinyl]amino]benzamide utilising 3-chloraniline (Fluka, Buchs, Switzerland)

$^1$H-NMR (400 MHz, DMSO-$d_6$, δ): 2.33 (s, 3H); 7.14 (m, 1H); 7.36 (m, 1H); 7.41 (d, 1H); 7.46 (d, 1H); 7.49 (ddd, 1H); 7.68-7.73 (m, 2H); 7.95 (m, 1H); 8.25 (m, 1H); 8.43 (m, 1H); 8.53 (d, 1H); 8.66 (dd, 1H); 9.15 (s, 1H); 9.26 (m, 1H); 10.33 (s, 1H).

Example 49

N-(2,2-Diphenylethyl)-4-methyl-3-[[4-(3-pyridinyl)-2-pyrimidinyl]amino]-benzamide utilising 2,2-diphenylethylamine (Aldrich, Buchs, Switzerland)

$^1$H-NMR (400 MHz, DMSO-$d_6$, δ): 2.24 (s, 3H); 3.87 (m, 2H); 4.41 (m, 1H); 7.12-7.17 (m, 2H); 7.23-7.31 (m, 9H); 7.41-7.44 (m, 2H); 7.51 (ddd, 1H); 7.97 (m, 1H); 8.37-8.44 (m, 2H); 8.48 (d, 1H); 8.68 (dd, 1H); 9.05 (s, 1H); 9.23 (m, 1H).

Example 50

N-(2,3-Dihydro-1H-inden-1-yl)-4-methyl-3-[[4-(3-pyridinyl)-2-pyrimidinyl]amino]-benzamide utilising 1-Aminoindane (Fluka, Buchs, Switzerland)

$^1$H-NMR (400 MHz, DMSO-$d_6$, δ): 1.90-2.01 (m, 1H); 2.29 (s, 3H); 2.43 (m, 1H); 2.77-2.86 (m, 1H); 2.91-2.98 (m, 1H); 5.56 (m, 1H); 7.08-7.25 (m, 4H); 7.31 (d, 1H); 7.43 (d, 1H); 7.50 (ddd, 1H); 7.64 (dd, 1H); 8.20 (m, 1H); 8.40 (m, 1H); 8.50 (d, 1H); 8.68-8.72 (m, 2H); 9.08 (s, 1H); 9.24 (m, 1H).

Example 51

N-(Diphenylmethyl)-4-methyl-3-[[4-(3-pyridinyl)-2-pyrimidinyl]amino]benzamide utilising alpha-aminodiphenylmethane (Fluka, Buchs, Switzerland)

$^1$H-NMR (400 MHz, DMSO-$d_6$, δ): 2.29 (s, 3H); 6.41 (d, 1H); 7.20-7.36 (m, 11H); 7.43 (d, 1H); 7.46 (ddd, 1H); 7.67 (dd, 1H); 8.18 (m, 1H); 8.38 (m, 1H); 8.50 (d, 1H); 8.68 (dd, 1H); 9.10 (s, 1H); 9.20 (d, 1H); 9.24 (m, 1H).

Example 52

4-Methyl-N-[2-(1-piperidinyl)ethyl]-3-[[4-(3-pyridinyl)-2-pyrimidinyl]amino]-benzamide utilising 1-(2-aminoethyl)piperidine (Aldrich, Buchs, Switzerland)

$^1$H-NMR (400 MHz, DMSO-$d_6$, δ): 1.30-1.38 (m, 2H); 1.41-1.48 (m, 4H); 2.28 (s, 3H); 2.31-2.41 (m, 6H); 3.33 (m, 2H); 7.31 (d, 1H); 7.44 (d, 1H); 7.51 (ddd, 1H); 7.55 (dd, 1H); 8.08 (m, 1H); 8.28 (t, 1H); 8.40 (m, 1H); 8.51 (d, 1H); 8.67 (dd, 1H); 9.07 (s, 1H); 9.24 (m, 1H).

Example 53

4-Methyl-3-[[4-(3-pyridinyl)-2-pyrimidinyl]amino]-N-(5,6,7,8-tetrahydro-1-naphthalenyl)benzamide utilising 5,6,7,8-tetrahydro-1-naphthylamine (Aldrich, Buchs, Switzerland)

$^1$H-NMR (400 MHz, DMSO-$d_6$, δ): 1.63-1.71 (m, 4H); 2.32 (s, 3H); 2.60 (m, 2H); 2.74 (m, 2H); 6.96 dd, 1H); 7.07-7.14 (m, 2H); 7.37 (d, 1H); 7.45 (d, 1H); 7.49 (ddd, 1H); 7.69 (dd, 1H); 8.25 (m, 1H); 8.41 (m, 1H); 8.52 (d, 1H); 8.67 (dd, 1H); 9.12 (s, 1H); 9.25 (m, 1H); 9.65 (br.s).

Example 54

4-Methyl-3-[[4-(3-pyridinyl)-2-pyrimidinyl]amino]-N-[[4-(trifluoromethyl)phenyl]-methyl]benzamide utilising 4-(trifluoromethyl)benzylamine (Aldrich, Buchs, Switzerland)

$^1$H-NMR (400 MHz, DMSO-d$_6$, δ): 2.30 (s, 3H); 4.53 (d, 2H); 7.34 (d, 1H); 7.44 (d, 1H); 7.46-7.53 (m, 3H); 7.62 (dd, 1H); 7.66 (m, 2H); 8.16 (m, 1H); 8.40 (m, 1H); 8.51 (d, 1H); 8.67 (dd, 1H); 9.08 (t, 1H); 9.10 (s, 1H); 9.24 (m, 1H).

Example 55

4-Methyl-N-[(5-methylpyrazinyl)methyl]-3-[[4-(3-pyridinyl)-2-pyrimidinyl]amino]-benzamide utilising 2-(aminomethyl)-5-methylpyrazine (TCI-JP, Distrib. Zürich, Switzerland).

$^1$H-NMR (400 MHz, DMSO-d$_6$, δ): 2.29 (s, 3H); 2.45 (s, 3H); 4.54 (d, 2H); 7.33 (d, 1H); 7.44 (d, 1H); 7.49 (ddd, 1H); 7.62 (dd, 1H); 8.14 (m, 1H); 8.40 (m, 1H); 8.45 (m, 2H); 8.50 (d, 1H); 8.66 (dd, 1H); 9.07 (t, 1H); 9.09 (s, 1H); 9.23 (m, 1H).

Example 56

N-(2-Ethoxyethyl)-4-methyl-3-[[4-(3-pyridinyl)-2-pyrimidinyl]amino]benzamide utilising 2-ethoxyethylamine (TCI-JP, Distrib. Zurich, Switzerland)

$^1$H-NMR (400 MHz, DMSO-d$_6$, δ): 1.07 (t, 3H); 2.28 (s, 3H); 3.30-3.49 (m, 6H); 7.31 (d, 1H); 7.43 (d, 1H); 7.51 (ddd, 1H); 7.57 (dd, 1H); 8.09 (m, 1H); 8.38-8.45 (m, 2H); 8.50 (d, 1H); 8.67 (dd, 1H); 9.07 (s, 1H); 9.24 (m, 1H).

Example 57

4-Methyl-N-[2-(2-oxo-1-imidazolidinyl)ethyl]-3-[[4-(3-pyridinyl)-2-pyrimidinyl]-amino]benzamide utilising 1-(2-aminoethyl)imidazolidin-2-one [Chem. Abstr. Reg. Number: 6281-42-1]

$^1$H-NMR (400 MHz, DMSO-d$_6$, δ): 2.27 (s, 3H); 3.13-3.22 (m, 4H); 3.30-3.40 (m, 4H); 6.27 (br.s, 1H); 7.30 (d, 1H); 7.43 (d, 1H); 7.49-7.56 (m, 2H); 8.08 (m, 1H); 8.40 (m, 1H); 8.45 (t, 1H); 8.50 (d, 1H); 8.67 (dd, 1H); 9.06 (s, 1H); 9.23 (m, 1H).

Example 58

4-Methyl-N-(5-methyl-2-pyridinyl)-3-[[4-(3-pyridinyl)-2-pyrimidinyl]amino]-benzamide utilising 2-amino-5-picoline (Aldrich, Buchs, Switzerland)

$^1$H-NMR (400 MHz, DMSO-d$_6$, δ): 2.26 (s, 3H); 2.32 (s, 3H); 7.35 (d, 1H); 7.45 (d, 1H); 7.49 (ddd, 1H); 7.64 (dd, 1H); 7.77 (dd, 1H); 8.07 (d, 1H); 8.18 (m, 1H); 8.31 (d, 1H); 8.43 (m, 1H); 8.52 (d, 1H); 8.66 (dd, 1H); 9.08 (m, 1H); 9.25 (m, 1H); 10.58 (s, 1H).

Example 59

1-[4-Methyl-3-[[4-(3-pyridinyl)-2-pyrimidinyl]amino]benzoyl]-4-phenyl-4-piperidinol utilising 4-hydroxy-4-phenylpiperidine (Aldrich, Buchs, Switzerland)

$^1$H-NMR (400 MHz, DMSO-d$_6$, δ): 1.45-1.73 (m, 2H); 1.88 (m, 2H); 2.28 (s, 3H); 3.15 (m, 1H); 3.47 (m, 1H); 3.64 (m, 1H); 4.39 (m, 1H); 5.14 (s, 1H); 7.14 (dd, 1H); 7.19 (m, 1H); 7.26-7.31 (m, 3H); 7.43 (d, 1H); 7.45-7.51 (m, 3H); 7.69 (d, 1H); 8.40 (m, 1H); 8.48 (d, 1H); 8.67 (dd, 1H); 9.03 (s, 1H); 9.24 (m, 1H).

Example 60

N-(3-Benzoylphenyl)-4-methyl-3-[[4-(3-pyridinyl)-2-pyrimidinyl]amino]benzamide utilising 3-aminobenzophenone (Aldrich, Buchs, Switzerland)

$^1$H-NMR (400 MHz, DMSO-d$_6$, δ): 2.32 (s, 3H); 7.39 (d, 1H); 7.43-7.58 (m, 6H); 7.67 (m, 1H); 7.70-7.77 (m, 3H); 8.13 (m, 1H); 8.20 (m, 1H); 8.27 (m, 1H); 8.42 (m, 1H); 8.52 (d, 1H); 8.66 (dd, 1H); 9.14 (s, 1H); 9.25 (m, 1H); 10.41 (s, 1H).

Example 61

N-[4-Methyl-3-[[4-(3-pyridinyl)-2-pyrimidinyl]amino]benzoyl]-glycine 1,1-dimethylethyl ester utilising glycine t-butyl ester hydrochloride (Aldrich, Buchs, Switzerland)

$^1$H-NMR (400 MHz, DMSO-d$_6$, δ): 1.40 (s, 9H); 2.29 (s, 3H); 3.86 (d, 2H); 7.33 (d, 1H); 7.43 (d, 1H); 7.51 (ddd, 1H); 7.58 (dd, 1H); 8.10 (d, 1H); 8.40 (m, 1H); 8.50 (d, 1H); 8.67 (dd, 1H); 8.75 (t, 1H); 9.08 (s, 1H); 9.23 (m, 1H).

Example 62

4-[[4-Methyl-3-[[4-(3-pyridinyl)-2-pyrimidinyl]amino]benzoyl]amino]benzene acetic acid ethyl ester utilising ethyl 4-aminophenylacetate (Maybridge Chemical Co. Ltd.)

$^1$H-NMR (400 MHz, DMSO-d$_6$, δ): 1.16 (t, 3H); 2.32 (s, 3H); 3.60 (s, 2H); 4.06 (q, 2H); 7.21 (m, 2H); 7.38 (d, 1H); 7.45 (d, 1H); 7.48 (ddd, 1H); 7.70 (m, 3H); 8.23 (m, 1H); 8.41 (m, 1H); 8.52 (d, 1H); 8.66 (dd, 1H); 9.13 (s, 1H); 9.25 (m, 1H); 10.16 (s, 1H).

Example 63

4-Methyl-N-[3-(methylphenylamino)propyl]-3-[[4-(3-pyridinyl)-2-pyrimidinyl]-amino]benzamide utilising N-(3-aminopropyl)-N-methylaniline (TCI-JP, Distrib. Zürich, Switzerland)

$^1$H-NMR (400 MHz, DMSO-d$_6$, δ): 1.73 (qui, 2H); 2.28 (s, 3H); 2.84 (s, 3H); 3.24-3.37 (m, 4H); 6.55 (m, 1H); 6.65 (m, 2H); 7.10 (m, 2H); 7.31 (d, 1H); 7.43 (d, 1H); 7.47 (ddd, 1H); 7.55 (dd, 1H); 8.10 (d, 1H); 8.37-8.44 (m, 2H); 8.50 (d, 1H); 8.65 (dd, 1H); 9.06 (s, 1H); 9.23 (m, 1H).

Example 64

1-[[3-[[4-Methyl-3-[[4-(3-pyridinyl)-2-pyrimidinyl]amino]benzoyl]amino]phenyl]methyl]-4-piperidinecarboxylic acid ethyl ester utilising ethyl 1-(3-aminobenzyl)piperidine-4-carboxylate (Maybridge Chemical Co. Ltd.)

$^1$H-NMR (400 MHz, DMSO-d$_6$, δ): 1.14 (t, 3H); 1.49-1.61 (m, 2H); 1.72-1.80 (m, 2H); 1.92-2.02 (m, 2H); 2.27 (m, 1H); 2.32 (s, 3H); 2.74 (m, 2H); 3.40 (s, 2H); 4.03 (q, 2H); 6.98 (d, 1H); 7.25 (m, 1H); 7.38 (d, 1H); 7.43-7.51 (m, 2H); 7.66-7.73 (m, 3H); 8.25 (s, 1H); 8.42 (m, 1H); 8.52 (d, 1H); 8.65 (dd, 1H); 9.12 (s, 1H); 9.25 (m, 1H); 10.14 (s, 1H).

Example 65

[[4-Methyl-3-[[4-(3-pyridinyl)-2-pyrimidinyl]amino]benzoyl]amino]propandioic acid diethyl ester utilising diethyl aminomalonate hydrochloride (Aldrich, Buchs, Switzerland)

$^1$H-NMR (400 MHz, DMSO-d$_6$, δ): 1.19 (t, 6H); 2.30 (s, 3H); 4.10-4.22 (m, 4H); 5.27 (d, 1H); 7.35 (d, 1H); 7.44 (d, 1H); 7.51 (ddd, 1H); 7.63 (dd, 1H); 8.15 (m, 1H); 8.40 (m, 1H); 8.50 (d, 1H); 8.67 (dd, 1H); 9.11 (s, 1H); 9.21-9.25 (m, 2H).

Example 66

N-[2-[bis(1-Methylethyl)amino]ethyl]-4-methyl-3-[[4-(3-pyridinyl)-2-pyrimidinyl]-amino]benzamide utilising 2-diisopropylamino-ethylamine (Fluka, Buchs, Switzerland)

$^1$H-NMR (400 MHz, DMSO-d$_6$, δ): 0.95 (m, 12H); 2.28 (s, 3H); 2.49 (m, 2H); 2.94 (m, 2H); 3.17 (m, 2H); 7.30 (d, 1H); 7.43 (d, 1H); 7.50 (ddd, 1H); 7.54 (dd, 1H); 8.09 (br.s, 1H); 8.27 (m, 1H); 8.40 (m, 1H); 8.50 (d, 1H); 8.67 (dd, 1H); 9.06 (s, 1H); 9.23 (m, 1H).

Example 67

N-[3-(Diethylamino)phenyl]-4-methyl-3-[[4-(3-pyridinyl)-2-pyrimidinyl]amino]-benzamide A solution containing ~50% of propylphosphonic anhydride in N,N-dimethylformamide (Fluka, Buchs, Switzerland; 674 μL, ~1.05 mmol) is added within 20 minutes to a stirred mixture of 4-methyl-3-[[4-(3-pyridinyl)-2-pyrimidinyl]amino]-benzoic acid (214.4 mg, 0.7 mmol), N,N-diethyl-1,3-benzenediamine (115 mg, 0.7 mmol) and triethylamine (776 μL, 5.6 mmol) in 2 mL N,N-dimethylformamide. After stirring for 24 hours at room temperature, the mixture is treated with a half-saturated aqueous solution of sodium hydrogen carbonate and extracted three times with ethyl acetate. The solvent is evaporated off under reduced pressure and the residue dried in vacuo. The crude product is purified by chromatography on silica gel, eluent 2% methanol in dichloromethane and crystallised from acetone to give the title compound as a crystalline solid. $^1$H-NMR (400 MHz, DMSO-d$_6$, δ): 1.07 (t, 6H); 2.31 (s, 3H); 3.29 (m, 4H); 6.38 (m, 1H); 7.06 (m, 2H); 7.11 (m, 1H); 7.36 (d, 1H); 7.43-7.50 (m, 2H); 7.67 (m, 1H); 8.21 (m, 1H); 8.43 (m, 1H); 8.51 (d, 1H); 8.66 (dd, 1H); 9.12 (s, 1H); 9.24 (m, 1H); 9.90 (s, 1H).

Example 68

4-Methyl-3-[[4-(3-pyridinyl)-2-pyrimidinyl]amino]-N-[[3-[(1-hydroxy-1-methyl-ethyl)]-5-(1,1,1-trifluoromethyl)phenyl]methyl]benzamide Diethylcyanophosphonate (Aldrich, Buchs, Switzerland; 0.33 mL, 2.0 mmol) is added to a stirred mixture of 4-methyl-3-[[4-(3-pyridinyl)-2-pyrimidinyl]amino]-benzoic acid (306 mg, 1.0 mmol), 3-[(1-hydroxy-1-methylethyl)]-5-(1,1,1-trifluoromethyl)benzeneamine (220 mg, 1.0 mmol) and triethylamine (560 μL, 4.0 mmol) in 5 mL N,N-dimethylformamide at 10° C. After stirring for 3 hours at 60° C., the mixture is treated with saturated aqueous solution of sodium hydrogen carbonate and extracted three times with ethyl acetate. The combined extracts are dried (MgSO$_4$), filtered and the solvent is evaporated off under reduced pressure to afford a crude product which is recrystallised from ethylacetate to give the title compound as a crystalline solid, m.p. 253-258° C.

Example 69

3-[[4-(3-Pyridinyl)-2-pyrimidinyl]amino]-N-[(4-methyl-1-piperazinyl)methyl]-benzamide Diethylcyanophosphonate (Aldrich, Buchs, Switzerland; 0.50 mL, 3.0 mmol) is added to a stirred mixture of 3-[[4-(3-pyridinyl)-2-pyrimidinyl]amino]-benzoic acid (438 mg, 1.5 mmol), 4-[(4-methyl-1-piperazinyl)methyl]benzeneamine (308 mg, 1.5 mmol) and triethylamine (840 μL, 3.0 mmol) in 10 mL N,N-dimethylformamide at 10° C. After stirring for 12 hours at 60° C., the mixture is treated with an aqueous solution of sodium hydrogen carbonate and extracted three times with ethyl acetate. The combined extracts are washed with water, and the solvent is evaporated off under reduced pressure to give a residue. The residue is resuspended in water and filtered to afford the crude product which is recrystallised from tetrahydrofuran-ethyl acetate to give N-[3-[[4-(3-Pyridinyl)-2-pyrimidinyl]amino]-N-[(4-methyl-1-piperazinyl)-methyl]benzamide as a crystalline solid, m.p. 220-224° C.

Example 69a

3-[(Aminoiminomethyl)amino]-4-methylbenzoic acid methyl ester mononitrate

Utilising the procedure described in Example 1a, but with 3-aminobenzoic acid methyl ester (Fluka, Buchs, Switzerland) in lieu of 3-amino-4-methylbenzoic acid ethyl ester, afforded the title compound as a crystalline solid, m.p. 170-172° C.

Example 69b

3-[[4-(3-Pyridinyl)-2-pyrimidinyl]amino]benzoic acid methyl ester

Utilising the procedure described in Example 1b, but with the intermediate of Example 69a in lieu of 4-methyl-3-[(aminoiminomethyl)amino]-4-methylbenzoic acid ethyl ester mononitrate, afforded the title compound as a crystalline solid, m.p. 195-200° C.

Example 69c

3-[[4-(3-Pyridinyl)-2-pyrimidinyl]amino]benzoic acid

Utilising the procedure described in Example 1c, but with the intermediate of Example 69b in lieu of 4-methyl-3-[[4-(3-pyridinyl)-2-pyrimidinyl]amino]benzoic acid ethyl ester, afforded the title compound as a crystalline solid, m.p. 285-293° C.

Example 70

3-[[4-(3-Pyridinyl)-2-pyrimidinyl]amino]-N-[(3-(1-hydroxy-1-methylethyl)-5-(1,1,1-trifluoromethyl)phenyl]benzamide Utilising the procedure described in Example 69, but with 3(1-hydroxy-1-methylethyl)-5-(1,1,1-trifluoromethyl)benzenamine in lieu of 4-[(4-methyl-1-piperazinyl)methyl]benzenamine, afforded 3-[[4-(3-pyridinyl)-2-pyrimidinyl]amino]-N-[(3-(1-hydroxy-1-methylethyl)-5-(1,1,1-trifluoromethyl)phenyl]benzamide as a crystalline solid, m.p. 213-215° C.

Example 71

4-Methyl-3-[[4-(3-pyridinyl)-2-pyrimidinyl]amino]-N-[3-[3-(1H-imidazol-1-yl)propoxy]-phenyl]benzamide Utilising the procedure described in Example 3, but employing 3-[3-(1H-imidazol-1-yl)propoxy]-benzenamine (Takao Nishi et al., JP 10182459) in lieu of 1-(2-pyridyl)piperazine, afforded the title compound as a solid.

$^1$H-NMR (400 MHz, DMSO-d$_6$, δ): 2.12-2.21 (m, 2H); 2.33 (s, 3H); 3.87 (t, 2H); 4.13 (t, 2H); 6.66 (dd, 1H); 6.87 (s, 1H); 7.15-7.26 (m, 2H); 7.32-7.42 (m, 2H); 7.44-7.52 (m, 3H); 7.61 (s, 1H); 7.70 (d, 1H); 8.24 (s, 1H); 8.43 (d, 1H); 8.53 (d, 1H); 8.67 (d, 1H); 9.13 (s, 1H); 9.26 (br. s, 1H); 10.13 (s, 1H).

Example 72

4-Methyl-3-[[4-(3-pyridinyl)-2-pyrimidinyl]amino]-N-[3-[2-(1H-imidazol-1-yl)ethoxy]phenyl]benzamide Utilising the procedure described in Example 3, but employing 3-[2-(1H-imidazol-1-yl)ethoxy]-benzenamine (Rolf Paul et al., Journal of Medicinal Chemistry (1993), 36(19), 2716-25) in lieu of 1-(2-pyridyl)piperazine, afforded the title compound as a crystalline solid.

$^1$H-NMR (400 MHz, DMSO-d$_6$, δ): 2.34 (s, 3H); 4.22 (t, 2H); 4.37 (t, 2H); 6.68 (dd, 1H); 6.90 (s, 1H); 7.21-7.27 (m, 2H); 7.36-7.43 (m, 2H); 7.46-7.53 (m, 3H); 7.67-7.74 (m, 2H); 8.25 (br. s, 1H); 8.44 (dt, 1H); 8.54 (d, 1H); 8.68 (dd, 1H); 9.15 (s, 1H); 9.27 (br. d, 1H); 10.15 (s, 1H).

Example 73

4-Methyl-3-[[4-(3-pyridinyl)-2-pyrimidinyl]amino]-N-[4-(ethylamino)-3-(trifluoromethyl)phenyl]benzamide Utilising the procedure described in Example 69, but employing N-ethyl-2-(trifluoromethyl)-1,4-benzenediamine in lieu of 3-[(1-hydroxy-1-methylethyl)]-5-(1,1,1-trifluoromethyl)-benzeneamine, afforded the title compound as a crystalline solid, m.p. 178-180° C.

The aniline is prepared as follows:

Example 73a

N-ethyl-2-(trifluoromethyl)-1,4-benzenediamine

A mixture of 2-bromo-5-nitrobenzotrifuoride (Lancaster Synthesis, GmbH; 5.4 g, 20 mmol) and a solution of ethylamine in ethanol (50 mL of 2M, 100 mmol) is heated at 80° C. for 18 hours in a steel pressure vessel. The mixture is then cooled and the solvent is evaporated off under reduced pressure to yield the crude product which is purified by column chromatography (silica gel, eluent 20% ethyl acetate in hexane) to afford N-ethyl-4-nitro-6-(trifluoromethyl)-benzenamine as yellow oil. This product is dissolved in ethanol (180 mL) and hydrogenated at atmospheric pressure over Raney nickel (0.5 g) at 45° C. The calculated amount of hydrogen is taken up in 50 hours. The mixture is then filtered and the solvent is evaporated off under reduced pressure to yield the crude product which is purified by chromatography (silica gel; eluent 50% ethyl acetate in hexane) and recrystallised from ether—hexane to give the title compound as a beige crystalline solid. $^1$H-NMR (400 MHz, DMSO-d$_6$): 1.11 (t, 3H), 3.05 (m, 2H), 4.18 (br t, 1H), 4.66 (br.s, 2H), 6.58-6.64 (m, 1H) and 6.68-6.75 (m, 2H).

Example 74

4-Methyl-3-[[4-(3-pyridinyl)-2-pyrimidinyl]amino]-N-[4-(diethylamino)-3-(trifluoromethyl)phenyl]benzamide Utilising the procedure described in Example 3, but employing N,N-diethyl-2-(trifluoromethyl)-1,4-benzenediamine (Toshio Niwa, DE 3524519) in lieu of 1-(2-pyridyl)piperazine, afforded the title compound as a crystalline solid, m.p. 128-131° C.

Example 75

(±)-4-Methyl-3-[[4-(3-pyridinyl)-2-pyrimidinyl]amino]-N-[4-[(2-hydroxy-propyl)amino]-3-(trifluoromethyl)phenyl]benzamide Utilising the procedure described in Example 3, but employing (±)-1-[[4-amino-2-(trifluoromethyl)phenyl]amino]-2-propanol (Tsutomu Mano, EP 299497) in lieu of 1-(2-pyridyl)piperazine, afforded the title compound as a crystalline solid, m.p. 184-186° C.

Example 76

4-Methyl-3-[[4-(3-pyridinyl)-2-pyrimidinyl]amino]-N-[4-[bis(2-methoxy-ethyl)amino]-3-(trifluoromethyl)phenyl]benzamide Utilising the procedure described in Example 3, but employing N,N-bis(2-methoxyethyl)-2-(trifluoromethyl)-1,4-benzenediamine (Toshio Niwa, DE 3524519) in lieu of 1-(2-pyridyl)piperazine, afforded the title compound as a crystalline solid, m.p. 156-157° C.

Example 77

4-Methyl-3-[[4-(3-pyridinyl)-2-pyrimidinyl]amino]-N-[4-(4-methyl-1-piperazinyl)-3-(trifluoromethyl)phenyl]benzamide Utilising the procedure described in Example 3, but employing 4-(4-methyl-1-piperazinyl)-3-(trifluoromethyl)-benzenamine (Anthony David Baxter, WO 0119800) in lieu of 1-(2-pyridyl)piperazine, afforded the title compound as a crystalline solid, m.p. 214-217° C.

Example 78

4-Methyl-3-[[4-(3-pyridinyl)-2-pyrimidinyl]amino]-N-[4-(1-piperidinyl)-3-(trifluoromethyl)phenyl]benzamide Utilising the procedure described in Example 3, but employing 4-(1-piperidinyl)-3-(trifluoromethyl)-benzenamine (Leping Li, WO 0151456) in lieu of 1-(2-pyridyl)piperazine, afforded the title compound as a crystalline solid, m.p. 201-202° C.

Example 79

4-Methyl-3-[[4-(3-pyridinyl)-2-pyrimidinyl]amino]-N-[4-(1-pyrrolidinyl)-3-(trifluoromethyl)phenyl]benzamide Utilising the procedure described in Example 3, but employing 4-(1-pyrrolidinyl)-3-(trifluoromethyl)-benzenamine (Steven Lee Bender WO 0153274) in lieu of 1-(2-pyridyl)piperazine afforded the title compound as a crystalline solid, m.p. 129-130° C.

Example 80

4-Methyl-3-[[4-(3-pyridinyl)-2-pyrimidinyl]amino]-N-[4-(4-morpholinyl)-3-(trifluoromethyl)phenyl]benzamide Utilising the procedure described in Example 69, but employing 4-(4-morpholinyl)-3-(trifluoromethyl)-benzenamine (Steven Lee Bender WO 0153274) in lieu of 3-[(1-hydroxy-1-methylethyl)]-5-(1,1,1-trifluoromethyl)benzeneamine, afforded the title compound as a crystalline solid, m.p. 216-218° C.

Example 81

4-Methyl-3-[[4-(3-pyridinyl)-2-pyrimidinyl]amino]-N-[4-phenyl-3-(trifluoromethyl)phenyl]benzamide Utilising the procedure described in Example 3, but employing 4-(phenyl)-3-(trifluoromethyl)-benzenamine in lieu of 1-(2-pyridyl)piperazine afforded the title compound as a crystalline solid, m.p. 172-174° C.

The aniline is prepared as follows:

Example 81a 4-(Phenyl)-3-(trifluoromethyl)benzenamine

Phenyl boronic acid (Aldrich, Buchs, Switzerland; 2.7 g, 22 mmol), Palladium II acetate (0.225 g, 1 mmol), tri-o-tolylphosphine (0.608 g, 2 mmol) and aqueous potassium carbonate solution (50 mL of 1 M) is added to a stirred solution of 2-bromo-5-nitrobenzotrifuoride (Lancaster Synthesis, GmbH; 5.4 g, 20 mmol) in dimethylformamide (200 mL) and heated at 120° C. under an argon atmosphere for 1 h. The mixture is then evaporated to dryness under reduced pressure and the residue is treated with water (100 mL) and extracted with ethyl acetate (3×80 mL). The combined extracts are washed (brine), dried (MgSO4), filtered and the solvent is evaporated off under reduced pressure to afford 4'-nitro-2'-(trifluoromethyl)-[1,1'-Biphenyl]. The biphenyl is dissolved in ethanol (200 mL) and hydrogenated at atmospheric pressure over Raney nickel (2 g) at 22° C. The calculated amount of hydrogen is taken up in 11 hours. The mixture is then filtered and the solvent is evaporated off under reduced pressure to yield the crude product which is purified by chromatography (silica gel; eluent ethyl acetate) to give the title compound as a brown oil. $^1$H-NMR (400 MHz, DMSO-$d_6$): 5.62 (br.s, 2H), 6.80 (dd, 1H), 6.96 (d, 1H), 6.99 (d, 1H), 7.19-7.23 (m, 2H), and 7.29-7.39 (m, 3H).

Example 82

4-Methyl-3-[[4-(3-pyridinyl)-2-pyrimidinyl]amino]-N-[3-[4-(3-pyridinyl)-3-(trifluoromethyl)phenyl]methyl]benzamide Utilising the procedure described in Example 69, but employing 4-(3-pyridinyl)-3-(trifluoromethyl)-benzenamine in lieu of 3-[(1-hydroxy-1-methylethyl)]-5-(1,1,1-trifluoromethyl)benzeneamine, afforded the title compound as a crystalline solid, m.p. 276-280° C.

The aniline is prepared as follows:

Example 82a 4-(3-Pyridinyl)-3-(trifluoromethyl)benzenamine

A stirred solution of 2-bromo-5-nitrobenzotrifuoride (Lancaster Synthesis, GmbH; 3.37 g, 12.5 mmol) and 3-(tri-n-butylstannyl)pyridine (Maybridge Chemical Co. Ltd., England; 5.0 g, 13.6 mmol) in xylene (75 mL) was purged with argon for 10 minutes at 20° C. Tetrakis(triphenylphosphine)palladium (0) (1.4 g, 1.25 mmol) is then added and the resulting mixture is heated at 130° C. for 24 hours under an argon atmosphere. The mixture is then cooled, treated with an aqueous solution of sodium hydroxide (150 mL of 0.1 M) and purged with air for 2 hours. The resulting mixture is then diluted with ethylacetate (200 mL) and filtered. The organic phase is then sequentially washed with water (2×80 mL) and saturated aqueous sodium chloride (1×80 mL), dried (MgSO$_4$), filtered and the solvent is evaporated off under reduced pressure to yield the crude product which is purified by column chromatography (silica gel, eluent 50% ethyl acetate in hexane) to afford 3-[(4-nitro-3-(trifluoromethyl)phenyl]pyridine. This product is dissolved in ethanol (200 mL) and hydrogenated at atmospheric pressure over Raney nickel (0.23 g) at 22° C. The calculated amount of hydrogen is taken up in 24 hours. The mixture is then filtered and the solvent is evaporated off under reduced pressure to yield the crude product which is purified by chromatography (silica gel; eluent 50% ethyl acetate in hexane) and recrystallised from ether—hexane to give the title compound as a colourless crystalline solid, m.p. 92-93° C.

Example 83

4-Methyl-3-[[4-(3-pyridinyl)-2-pyrimidinyl]amino]-N-[4-(1H-imidazol-1-yl)-3-(trifluoromethyl)phenyl]benzamide Utilising the procedure described in Example 3, but employing 4-(1H-imidazol-1-yl)-3-(trifluoromethyl)-benzenamine (Steven Lee Bender WO 0153274) in lieu of 1-(2-pyridyl)piperazine afforded the title compound as a crystalline solid, m.p. 226229° C.

Example 84

4-Methyl-3-[[4-(3-pyridinyl)-2-pyrimidinyl]amino]-N-[4-(2,4-dimethyl-1H-imidazol-1-yl)-3-(trifluoromethyl)phenyl]benzamide Utilising the procedure described in Example 69, but employing 4-(2,4-dimethyl-1H-imidazol-1-yl)-3-(trifluoromethyl)-benzenamine in lieu of 3-[(1-hydroxy-1-methylethyl)]-5-(1,1,1-trifluoromethyl)benzenamine, afforded the title compound as an amorphous solid.

The aniline is prepared as follows:

Example 84a 4-(2,4-dimethyl-1H-imidazol-1-yl)-3-(trifluoromethyl)-benzenamine A mixture of 2-bromo-5-nitrobenzotrifuoride (Lancaster Synthesis, GmbH; 6.0 g, 22 mmol) and 2,4-dimethylimidazol (10.6, 110 mmol) is heated at 120° C. for 36 hours under an argon atmosphere. The mixture is then cooled and the residue is treated with water (150 mL) and extracted with ethyl acetate (3×80 mL). The combined extracts are washed (brine), dried ($MgSO_4$), filtered and the solvent is evaporated off under reduced pressure to yield the crude product which is purified by column chromatography (silica gel, eluent ethyl acetate) to afford 1-[4-nitro-2-(trifluoromethyl)phenyl]-1H-imidazole as yellow crystalline solid. This product is dissolved in ethanol (290 mL) and hydrogenated at atmospheric pressure over Raney nickel (1.15 g) at 25° C. The calculated amount of hydrogen is taken up in 14 hours. The mixture is then filtered and the solvent is evaporated off under reduced pressure to yield the crude product which is purified by recrystallisation from ether—hexane to give the title compound as a crystalline solid, m.p. 163-164° C.

Example 85

4-Methyl-3-[[4-(3-pyridinyl)-2-pyrimidinyl]amino]-N-[4-(4-methyl-1H-imidazol-1-yl)-3-(trifluoromethyl)phenyl]benzamide Utilising the procedure described in Example 69, but employing 4-(4-methyl-1H-imidazol-1-yl)-3-(trifluoromethyl)-benzenamine in lieu of 3-[(1-hydroxy-1-methylethyl)]-5-(1,1,1-trifluoromethyl)benzenamine, afforded the title compound as a crystalline solid, m.p. 154-163° C.

The aniline is prepared as follows:

Example 85a 4-(4-Methyl-1H-imidazol-1-yl)-3-(trifluoromethyl)-benzenamine

Utilising the procedure described in Example 84a, but employing 4(5)-methyl-1H-imidazole in lieu of 2,4-dimethylimidazol, afforded the title compound as a beige crystalline solid, m.p. 141-143° C.

Example 86

4-Methyl-3-[[4-(3-pyridinyl)-2-pyrimidinyl]amino]-N-[4-(2-methyl-1H-imidazol-1-yl)-3-(trifluoromethyl)phenyl]benzamide Utilising the procedure described in Example 69, but employing 4-(2-methyl-1H-imidazol-1-yl)-3-(trifluoromethyl)-benzenamine in lieu of 3-[(1-hydroxy-1-methylethyl)]-5-(1,1,1-trifluoro methyl)benzeneamine, afforded the title compound as a crystalline solid, m.p. 154-163° C.

The aniline is prepared as follows:

Example 86a 4-(2-Methyl-1H-imidazol-1-yl)-3-(trifluoromethyl)-benzenamine

Utilising the procedure described in Example 84a, but employing 2-methyl-1H-imidazole in lieu of 2,4-dimethylimidazole, afforded the title compound as a colourless crystalline solid, m.p. 117-119° C.

Example 87

4-Methyl-3-[[4-(3-pyridinyl)-2-pyrimidinyl]amino]-N-[3-(4-morpholinyl)-5-[(methylamino)carbonyl]phenyl]benzamide Utilising the procedure described in Example 69, but employing 3-amino-5-(4-morpholinyl)-N-(methyl)-benzamide in lieu of 3-[(1-hydroxy-1-methylethyl)]-5-(1,1,1-trifluoromethyl)-benzenamine, afforded the title compound as a crystalline solid, m.p. 153-156° C.

The aniline is prepared as follows:

Example 87a

3-Bromo-5-nitro-benzoic acid, 1,1-dimethylethyl ester

A solution of n-butyllithium in hexane (12.8 mL of 2.5 M, 32 mmol) is added with stirring to t-butanol (46 mL) at 25° C. under an argon atmosphere. After 30 min the mixture is treated dropwise with a solution of 3-bromo-5-nitro-benzoyl chloride (J. Mindl, Collect. Czech. Chem. Commun. (1973), 38, 3496-505; 32 mmol) in dry THF (40 mL) and stirred for a further 17 h. The mixture is then treated with ether (250 mL) and washed with brine. The ether solution was dried ($MgSO_4$) and the solvent is evaporated off under reduced pressure to give the crude product which is purified by column chromatography (silica gel, eluent 20% ethyl acetate in hexane) and recrystallised from ether—hexane to afford the title compound as colourless crystalline solid, m.p. 77-78° C.

Example 87b 3-(4-Morpholinyl)-5-nitro-benzoic acid, 1,1-dimethylethyl ester

A stirred mixture of 3-bromo-5-nitro-benzoic acid, 1,1-dimethylethyl ester (example 86a; 3.02 g, 10 mmol) and morpholine (1.22 mL, 14 mmol) in toluene (50 mL) is treated with sodium t-butylate (1.34 g, 14 mmol), tri-t-butylphosphine (3 mL, 1.5 mmol) and tris-(dibenzylidene acetone) dipalladium[0] (0.45 g, 0.5 mmol) under an argon atmosphere, and then heated at 60° C. for 18 h. The mixture is diluted with ethyl acetate (150 mL), filtered, washed with brine (2×50 mL), dried ($MgSO_4$) and the solvent is evaporated off under reduced pressure to give the crude product which is purified by column chromatography (silica gel, eluent 15% ethyl acetate in hexane) and recrystallised from ethyl acetate—hexane to afford the title compound as colourless crystalline solid, m.p. 116-118° C.

Example 87c 3-(4-Morpholinyl)-5-nitro-benzoic acid, methyl ester

A mixture of 3-(4-morpholinyl)-5-nitro-benzoic acid, 1,1-dimethylethyl ester (Example 87b; 0.77 g, 2.5 mmol), 1,8-diazabicyclo[5,4,0]undec-7-ene (0.56 mL, 3.75 mL), and potassium bromide (1.09 g, 12.5 mmol) in methanol (25 mL) is stirred at 90° C. for 250 min. The cooled mixture is then added to hydrochloric acid (50 mL of 0.1 M) and extracted with ethyl acetate (3×100 mL). The combined extracts are washed with saturated aqueous sodium hydro-carbonate (2×25 mL), water (2×25 mL) and brine (2×50 mL), dried ($MgSO_4$) and the solvent is evaporated off under reduced pressure to give the crude product which is purified by recrystallisation from ethyl acetate—hexane to afford the title compound as yellow crystalline solid.

Example 87d 3-(4-Morpholinyl)-5-nitro-N-(methyl)-benzamide

A stirred solution of 3-(4-morpholinyl)-5-nitro-benzoic acid, methyl ester (Example 86c; 0.53 g, 2 mmol) in toluene (5 mL) under an argon atmosphere, is treated with a mixture of methylamine hydrochloride (0.27 g, 4 mmol), triethylaluminium (2 mL of a 2 M solution in toluene, 4 mmol) in toluene (5 mL) and heated at 60° C. for 18 h. The cooled mixture is then treated with hydrochloric acid (10 mL of 2 M), stirred for 5 min and then treated with aqueous sodium hydroxide (5 mL of 4 M). The mixture is then treated with water (100 mL) and extracted with ethyl acetate (3×100 mL). The combined extracts are washed with brine (2×50 mL), dried ($MgSO_4$) and the solvent is evaporated off under reduced pressure to give the crude product which is purified by recrystallisation from ethyl acetate to afford the title compound as yellow crystalline solid, m.p. 204-207° C.

Example 87e

3-Amino-5-(4-Morpholinyl)-N-(methyl)-benzamide

A solution of 3-(4-morpholinyl)-5-nitro-N-(methyl)-benzamide (Example 86d; 300 mg, 1.12 mmol) in ethanol (20 mL) is hydrogenated at atmospheric pressure over Raney nickel (0.2 g) at 25° C. The calculated amount of hydrogen is taken up in 19 hours. The mixture is then filtered and the solvent is evaporated off under reduced pressure to yield the crude product which is purified by recrystallisation from ethyl acetate to give the title compound as a beige crystalline solid, m.p. 201-204° C.

Example 88

4-Methyl-3-[[4-(3-pyridinyl)-2-pyrimidinyl]amino]-N-[3-[(methylamino)carbonyl]-5-(trifluoromethyl)phenyl]benzamide Utilising the procedure described in Example 69, but employing 3-amino-5-(trifluoromethyl)-N-(methyl)-benzamide in lieu of 3-[(1-hydroxy-1-methylethyl)]-5-(1,1,1-trifluoromethyl)-benzeneamine, afforded the title compound as a crystalline solid, m.p. 245-249° C.

Example 88a

3-Amino-5-(trifluoromethyl)-N-(methyl)-benzamide

Utilising the procedure described in Example 86e, but employing α,α,α-trifluoro-N-methyl-5-nitro-m-toluamide (Dean E. Welch, J. Med. Chem. (1969), 12, 299-303) in lieu of 3-(4-morpholinyl)-5-nitro-N-(methyl)-benzamide, afforded the title compound as a beige crystalline solid, m.p. 113-115° C.

Example 89

4-Methyl-3-[[4-(3-pyridinyl)-2-pyrimidinyl]amino]-N-[5-(3-pyridinyl)-3-(trifluoromethyl)phenyl]benzamide Utilising the procedure described in Example 69, but employing 5-(3-pyridinyl)-3-(trifluoromethyl)-benzenamine in lieu of 3-[(1-hydroxy-1-methylethyl)]-5-(1,1,1-trifluoromethyl)-benzeneamine, afforded the title compound as a crystalline solid, m.p. 275-279° C.

The aniline is prepared as follows:

Example 89a 5-(3-Pyridinyl)-3-(trifluoromethyl)benzenamine

A stirred solution of 3-amino-5-bromo-benzotrifluoride (Apollo, England; 1.12 g, 5 mmol) and 3-(tri-n-butylstannyl)pyridine (Maybridge Chemical Co. Ltd., England; 2.0 g, 5.4 mmol) in xylene (30 mL) was purged with argon for 10 minutes at 20° C. Tetrakis(triphenylphosphine)-palladium (0) (1.16 g, 1.0 mmol) is then added and the resulting mixture is heated at 140° C. for 36 hours under an argon atmosphere. The mixture is then cooled, treated with an aqueous solution of sodium hydroxide (100 mL of 0.1 M) and purged with air for 2 hours. The resulting mixture is then diluted with ethylacetate (200 mL) and filtered. The organic phase is then sequentially washed with water (2×80 mL) and saturated aqueous sodium chloride (1×80 mL), dried ($MgSO_4$), filtered and the solvent is evaporated off under reduced pressure to yield the crude product which is purified by column chromatography (silica gel, eluent ethyl acetate) to afford the title compound as a brown oil. $^1$H-NMR (400 MHz, DMSO-$d_6$, δ): 5.73 (br s, 2H), 6.83 (dd, 1H), 6.99 (d, 1H), 7.04 (d, 1H), 7.39 (dd, 1H), 7.64 (d, 1H), 8.42 (m, 1H) and 8.53 (dd, 1H).

Example 90

4-Methyl-3-[[4-(3-pyridinyl)-2-pyrimidinyl]amino]-N-[5-(4-morpholinyl)-3-(trifluoromethyl)phenyl] benzamide Utilising the procedure described in Example 69, but employing 5-(4-morpholinyl)-3-(trifluoromethyl)-benzenamine in lieu of 3-[(1-hydroxy-1-methylethyl)]-5-(1,1,1-trifluoro-methyl)benzenamine, afforded the title compound as a crystalline solid, m.p. 208-211° C.

The aniline is prepared as follows:

Example 90a

[3-Bromo-5-(trifluoromethyl)phenyl]-carbamic acid, 1,1-dimethylethyl ester

A mixture of 3-amino-5-bromo-benzotrifluoride (Apollo, England; 12 g, 50 mmol), di-t-butyl-dicarbonate (12 g, 55 mmol) and 4-dimethylaminopyridine (0.61 g, 5 mmol) in acetonitrile (100 mL) is stirred at 60° C. for 8 h. The solvent is then evaporated off under reduced pressure to yield the crude product which is purified by column chromatography (silica gel, eluent 10% ethyl acetate in hexane) and recrystallised from hexane to afford the title compound as a colourless crystalline solid, m.p. 113-115° C.

Example 90b

[3-(4-Morpholinyl)-5-(trifluoromethyl)phenyl]-carbamic acid, 1,1-dimethylethyl ester Utilising the procedure described in Example 86b but employing [3-bromo-5-(trifluoromethyl)-phenyl]carbamic acid, 1,1-dimethylethyl ester (Example 90a) in lieu of 3-bromo-5-nitro benzoic acid, 1,1-dimethylethyl ester, afforded the title compound as a crystalline solid, m.p. 146-148° C.

Example 90c

5-(4-Morpholinyl)-3-(trifluoromethyl)-benzenamine

[3-(4-morpholinyl)-5-(trifluoromethyl)phenyl]-carbamic acid, 1,1-dimethylethyl ester (Example 90b; 1.7 g, 5 mmol) is treated with a solution of hydrogen chloride in isopropanol (30 mL of 4 M) and heated at 60° C. for 5 h. The solvent is evaporated off under reduced pressure and the residue is treated with aqueous sodium hydrogen carbonate solution (80 mL) and extracted with ethyl acetate (3×80 mL). The combined extracts are washed with brine (2×50 mL), dried (MgSO$_4$) and the solvent is evaporated off under reduced pressure to give the crude product which is purified by recrystallisation from ether—hexane to afford the title compound as yellow crystalline solid, m.p. 96-97° C.

Example 91

4-Methyl-3-[[4-(3-pyridinyl)-2-pyrimidinyl]amino]-N-[5-(2-methyl-1H-imidazol-1-yl)-3-(trifluoromethyl)phenyl]benzamide Utilising the procedure described in Example 69, but employing 5-(2-methyl-1H-imidazol-1-yl)-3-(trifluoromethyl)-benzenamine in lieu of 3-[(1-hydroxy-1-methylethyl)]-5-(1,1,1-trifluoro-methyl)benzeneamine, afforded the title compound as a crystalline solid, m.p. 242-247° C.

The was aniline is prepared as follows:

Example 91a

3-(2-Methyl-1H-imidazol-1-yl)-5-(trifluoromethyl)-benzonitrile

A mixture of 3-fluoro-5-(trifluoromethyl)-benzonitrile (Lancaster Synthesis GmbH; 17 g, 89 mmol) and 2-methylimidazole (Fluka, Buchs, Switzerland; 22.2 g, 270 mmol) in N,N-dimethylacetamide (80 mL) is stirred at 145° C. for 19 h. The solvent is evaporated off under reduced pressure and the residue is dissolved in ethyl acetate (200 mL). The solution is washed with brine (200 mL), dried (Na$_2$SO$_4$) and the solvent is evaporated off under reduced pressure to give the crude product which is purified by recrystallisation from ether—hexane to afford the title compound as yellow crystalline solid, m.p. 132-134° C.

Example 91b

3-(2-Methyl-1H-imidazol-1-yl)-5-(trifluoromethyl)-benzoic acid

A solution of 3-(2-methyl-1H-imidazol-1-yl)-5-(trifluoromethyl)-benzonitrile (Example 91a; 16.7 g, 66 mmol) in dioxane (300 mL) is added to an aqueous solution of sodium hydroxide (275 mL of 1 M) and the mixture is heated at 95° C. for 18 h. The solvent is evaporated off under reduced pressure and the residue is neutralised with hydrochloric acid (1 M) and extracted with butanol (2×250 mL). The solvent is evaporated of under reduced pressure to give the title compound. $^1$H-NMR (400 MHz, DMSO-d$_6$, δ): 7.17 (s, 1H); 8.03 (s, 1H); 8.12 (s, 1H); 8.35 (s, 1H); 8.41 (s, 1H); 8.53 (s, 1H); 13.90 (br., 1H).

Example 91c

[3-(2-methyl-1H-imidazol-1-yl)-5-(trifluoromethyl) phenyl]-carbamic acid, 1,1-dimethylethyl ester Triethylamine (5.23 mL, 37.5 mmol) is added to a stirred suspension of 3-(2-methyl-1H-imidazol-1-yl)-5-(trifluoromethyl)-benzoic acid (Example 91b; 6.8 g, 25 mmol) in t-butanol (200 mL). Diphenylphosphorylazide (7.6 g, 27.5 mmol) is added to the resulting solution and the mixture is heated 80° C. for 16 h. The solvent is evaporated off under reduced pressure and the residue is treated with water (100 mL) and extracted with ethyl acetate (2×100 mL). The combined extracts are washed with brine (100 mL), dried (Na$_2$SO$_4$) and the solvent is evaporated off under reduced pressure to give the crude product which is purified by column chromatography (silica gel, eluent 2% ethanol in ethyl acetate) and recrystallised from ether-hexane to afford the title compound as a colourless crystalline solid, m.p. 203-208° C.

Example 91d

5-(2-Methyl-1H-imidazol-1-yl)-3-(trifluoromethyl)-benzenamine

Utilising the procedure described in Example 90c but employing [3-(2-methyl-1H-imidazol-1-yl)-5-(trifluoromethyl)phenyl]-carbamic acid, 1,1-dimethylethyl ester (Example 91c) in lieu of [3-(4-morpholinyl)-5-(trifluoromethyl)

Example 92

4-Methyl-3-[[4-(3-pyridinyl)-2-pyrimidinyl]amino]-N-[5-(4-methyl-1H-imidazol-1-yl)-3-(trifluoromethyl)phenyl]benzamide Utilising the procedure described in Example 69, but employing 5-(4-methyl-1H-imidazol-1-yl)-3-(trifluoromethyl)-benzenamine in lieu of 3-[(1-hydroxy-1-methylethyl)]-5-(1,1,1-trifluoro-methyl)benzeneamine, afforded the title compound as a crystalline solid, m.p. 235-236° C.

The was aniline is prepared as follows:

Example 92a 3-(4-Methyl-1H-imidazol-1-yl)-5-(trifluoromethyl)-benzonitrile

Utilising the procedure described in Example 91a, but employing 4-methyl-1H-imidazole in lieu of 2-methylimidazole, afforded the title compound as a crystalline solid, m.p. 127-128° C.

Example 92b 3-(4-Methyl-1H-imidazol-t-yl)-5-(trifluoromethyl)-benzoic acid

Utilising the procedure described in Example 91b, but employing 3-(4-methyl-1H-imidazol-1-yl)-5-(trifluoromethyl)-benzonitrile (Example 92a) in lieu of 3-(2-methyl-1H-imidazol-1-yl)-5-(trifluoromethyl)-benzonitrile, afforded the title compound as a crystalline solid, m.p. >300° C.

Example 92c

[3-(4-Methyl-1H-imidazol-1-yl)-5-(trifluoromethyl)phenyl]-carbamic acid, 1,1-dimethylethyl ester Utilising the procedure described in Example 91c, but employing 3-(4-methyl-1H-imidazol-1-yl)-5-(trifluoromethyl)-benzoic acid (Example 92b) in lieu of 3-(2-methyl-1H-imidazol-1-yl)-5-(trifluoromethyl)-benzoic acid, afforded the title compound as a crystalline solid, m.p. 186-188° C.

Example 92d 5-(2-Methyl-1H-imidazol-1-yl)-3-(trifluoromethyl)-benzenamine

Utilising the procedure described in Example 91d, but employing [3-(4-methyl-1H-imidazol-1-yl)-5-(trifluoromethyl)phenyl]-carbamic acid, 1,1-dimethylethyl ester (Example 92c) in lieu of [3-(2-methyl-1H-imidazol-1-yl)-5-(trifluoromethyl)phenyl]-carbamic acid, 1,1-dimethylethyl ester, afforded the title compound as a colourless crystalline solid, m.p. 127-131° C.

Example 93

4-Methyl-3-[[4-(3-pyridinyl)-2-pyrimidinyl]amino]-N-[5-(5-methyl-1H-imidazol-1-yl)-3-(trifluoromethyl)phenyl]benzamide Utilising the procedure described in Example 3, but employing 5-(5-methyl-1H-imidazol-1-yl)-3-(trifluoromethyl)-benzenamine in lieu of 1-(2-pyridyl)piperazine, afforded the title compound as a crystalline solid, m.p. 231-233° C.

The aniline is prepared as follows:

Example 93a 3-(5-Methyl-1H-imidazol-1-yl)-5-(trifluoromethyl)-benzonitrile

Utilising the procedure described in Example 91a, but employing 4-methyl-1H-imidazole in lieu of 2-methylimidazole, afforded the title compound as a crystalline solid, m.p. 99-101° C.

Example 93b 3-(5-Methyl-1H-imidazol-1-yl)-5-(trifluoromethyl)-benzoic acid

Utilising the procedure described in Example 91b, but employing 3-(5-methyl-1H-imidazol-1-yl)-5-(trifluoromethyl)-benzonitrile (Example 93a) in lieu of 3-(2-methyl-1H-imidazol-1-yl)-5-(trifluoromethyl)-benzonitrile, afforded the title compound as a colourless crystalline solid, m.p. 243-245° C.

Example 93c

[3-(5-Methyl-1H-imidazol-1-yl)-5-(trifluoromethyl)phenyl]-carbamic acid, 1,1-dimethylethyl ester Utilising the procedure described in Example 91c, but employing 3-(5-methyl-1H-imidazol-1-yl)-5-(trifluoromethyl)-benzoic acid (Example 93b) in lieu of 3-(2-methyl-1H-imidazol-1-yl)-5-(trifluoromethyl)-benzoic acid, afforded the title compound as a crystalline solid, m.p. 169-171° C.

Example 93d 5-(5-Methyl-1H-imidazol-1-yl)-3-(trifluoromethyl)-benzenamine

Utilising the procedure described in Example 91d, but employing [3-(5-methyl-1H-imidazol-1-yl)-5-(trifluoromethyl)phenyl]-carbamic acid, 1,1-dimethylethyl ester (Example 93c) in lieu of [3-(2-methyl-1H-imidazol-1-yl)-5-(trifluoromethyl)phenyl]-carbamic acid, 1,1-dimethylethyl ester, afforded the title compound as a colourless crystalline solid, m.p. 131-133° C.

Example 94

4-Methyl-3-[[4-(3-pyridinyl)-2-pyrimidinyl]amino]-N-[3-(4-methyl-1-piperazinyl)-5-(trifluoromethyl)phenyl]benzamide Utilising the procedure described in Example 69, but employing 3-(4-methyl-1-piperazinyl)-5-(trifluoromethyl)-benzenamine in lieu of 3-[(1-hydroxy-1-methylethyl)]-5-(1, 1,1-trifluoro methyl)benzeneamine, afforded the title compound as a crystalline solid, m.p. 192-194° C.

The aniline is prepared as follows:

Example 94a

[3-(4-methyl-1-piperazinyl)-5-(trifluoromethyl)phenyl]-carbamic acid, 1,1-dimethylethyl ester Utilising the procedure described in Example 87b, but employing 1-methyl-1-piperazine in lieu of morpholine, afforded the title compound as a crystalline solid, m.p. 225° C.

Example 94b 3-(4-methyl-1-piperazinyl)-5-(trifluoromethyl)-benzenamine

Utilising the procedure described in Example 90c, but employing [3-(4-methyl-1-piperazinyl)-5-(trifluoromethyl)phenyl]-carbamic acid, 1,1-dimethylethyl ester (Example 94a) in lieu of [3 (4-morpholinyl)-5-(trifluoromethyl)phenyl]-carbamic acid, 1,1-dimethylethyl ester, afforded the title compound as oil. $^1$H-NMR (400 MHz, DMSO-$d_6$): 2.20 (s, 3H), 2.42 (m, 4H), 3.07 (m, 4H), 3.32 (br s, 2H), 5.34 (s, 1H) and 6.31 (s, 2H).

Example 95

4-Methyl-3-[[4-(3-pyridinyl)-2-pyrimidinyl]amino]-N-[2-(1-pyrrolidinyl)-5-(trifluoromethyl)phenyl]benzamide Utilising the procedure described in Example 3, but employing 2-(1-pyrrolidinyl)-5-(trifluoromethyl)-benzenamine (Lancaster Synthesis Ltd.; Yasuhiro Ohtake et al., WO 9965874) in lieu of 1-(2-pyridyl)piperazine, afforded the title compound as a crystalline solid.

$^1$H-NMR (400 MHz, DMSO-$d_6$): 1.77-1.82 (m, 4H); 2.34 (s, 3H); 3.31-3.37 (m, 4H); 6.86 (d, 1H); 7.34-7.44 (m, 2H); 7.47 (d, 1H); 7.49-7.53 (m, 1H); 7.73 (dd, 1H); 8.27 (d, 1H); 8.43 (dt, 1H); 8.53 (d, 1H); 8.69 (dd, 1H); 9.13 (s, 1H); 9.27 (d, 1H); 9.96 (s, 1H).

Example 96

3-[[4-(3-pyridinyl)-2-pyrimidinyl]amino]-N-[5-(4-methyl-1H-imidazol-1-yl)-3-(trifluoromethyl)phenyl]benzamide Utilising the procedure described in example 1, but employing 3-[[4-(3-pyridinyl)-2-pyrimidinyl]amino]-benzoic acid in lieu of 4-methyl-3-[[4-(3-pyridinyl)-2-pyrimidinyl]amino]-benzoic acid and 5-(4-methyl-1H-imidazol-1-yl)-3-(trifluoromethyl)-benzenamine in lieu of furfurylamine, afforded the title compound as pale-yellow crystalline solid, m.p. 264-266° C.

Example 96a

3-[(Aminoiminomethyl)amino]-benzoic acid ethyl ester mononitrate

Utilising the procedure described in example 1a but employing 3-amino-benzoic acid ethyl ester (Fluka, Buchs, Switzerland) in lieu of 3-amino-4-methylbenzoic acid ethyl ester, afforded the title compound as a crystalline solid, m.p. 170-172° C.

Example 96b

3-[[4-(3-pyridinyl)-2-pyrimidinyl]amino]-benzoic acid ethyl ester

Utilising the procedure described in example 1b but employing 3-[(aminoiminomethyl)amino]-benzoic acid ethyl ester mononitrate in lieu of 3-[(aminoiminomethyl)amino]-4-methyl-benzoic acid ethyl ester mononitrate, afforded the title compound as a crystalline solid, m.p. 197-199° C.

Example 96c

3-[[4-(3-pyridinyl)-2-pyrimidinyl]amino]-benzoic acid

Utilising the procedure described in example 1c but employing 3-[[4-(3-pyridinyl)-2-pyrimidinyl]amino]-benzoic acid ethyl ester in lieu of 4-methyl-3-[[4-(3-pyridinyl)-2-pyrimidinyl]amino]-benzoic acid ethyl ester, afforded the title compound as a crystalline solid, m.p. 291-295° C.

Example 97

Soft Capsules 5000 soft gelatin capsules, each comprising as active ingredient 0.05 g of one of the compounds of formula I mentioned in the preceding Examples, are prepared as follows: 250 g pulverized active ingredient is suspended in 2L Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

Example 98

Pharmacokinetic Data

The compound of formula I to be tested is formulated for administration to female OF1 mice from IFACREDO, France, by first dissolving in NMP, and then by diluting with PEG300 to a final concentration of 10% v/v NMP: 90% v/v PEG300, producing a clear solution of the compound. The concentrations were adjusted to deliver a constant volume of 10 mL/kg body weight. The compound is prepared immediately before use. The formulated compound is administered perorally by gavage to provide dosages of 50 mg/kg. At the allotted time points mice (4 at each time) are anesthetized with 3% isoflurane in medical oxygen and blood samples are obtained by heart puncture into heparinized tubes (ca. 30 IU/mL). The animals are subsequently killed without recovering from the anesthetic. Plasma is prepared from the blood by centrifugation (10,000 g, 5 min) and either analyzed immediately or stored frozen at −70° C.

The plasma samples (10-250 μL) are e.g. spiked with 5 μL of internal standard, mixed with 200 μL 0.1 M NaOH and 500 μL chloroform in a 1.5 mL Eppendorf tube and shaken vigorously for 10 minutes on an Eppendorf mixer. Thereafter, the mixture is centrifuged (3 min at 10'000×g), the organic phase transferred to a second Eppendorf tube and evaporated to dryness in a vacuum centrifuge (Speedvac 5301). The dry residue e.g. is dissolved in 250 µL of 10% v/v Acetonitrile in water containing 0.1% formic acid. The subsequent analysis is carried out e.g. by HPLC/MS-MS using an Agilent 1100 Series (Agilent, Palo Alto, Calif., USA) HPLC system with vacuum degasser, binary pump, and thermostated column compartment combined with a cooled autosampler system (HTS PAL, CTC Analytics, Zwingen, Switzerland). The sample (5-15 µL) is injected e.g. onto an Ultra Phenyl column (particle size 3 µm, 50×1 mm; Restek, Bellefonte, USA) with a guard column (4×2 mm) of the same material (Phenomenex, Torrance, USA). After equilibration e.g. with water and a latency period of 1 min the sample is eluted e.g. by a linear gradient of 0-100% acetonitrile in water containing 0.2% v/v formic acid over a period of 11 min at a flow rate of 60 µL/min. The column is prepared for the next sample e.g. by re-equilibrating for 3 min with 100% water to the starting conditions. The separation is performed e.g. at a column temperature of 40° C. The column effluent is introduced e.g. directly into the ion source of a triple stage quadropole mass spectrometer (Quattro Ultima™, Micromass, Manchester, UK) controlled by Masslynx™ 3.5 software (Micromass, Manchester, UK) using as ionization technique electrospray ionization positive mode (ESI+). The compound is detected by MS/MS following fragmentation of the parent ions. The limit of quantitation is determined at e.g. 0.002 nmol/L. A calibration curve is constructed with known amounts of compound including a fixed amount of internal standard in plasma which is processed as described above. The concentration of unknown samples is calculated from a plot of the peak area ratio of the selected daughter ion of the analyte to the product of its internal standard (ordinate) against the nominal concentration (abscissa). Regression analysis is performed using Quanlynx™, Masslynx™ software 3.5 (Micromass, Manchester, UK).

Example 99

In Vitro Inhibition Data

Enzymatic (c-Abl, KDR, Flt3) in vitro inhibition data are presented as % inhibition at 10 µM. The measurements are made as described above in the general description.

| Example | Abl % @ 10 µM | KDR % @ 10 µM | Flt3% @ 10 µM |
|---|---|---|---|
| 1 | 51 | 57 | |
| 2 | 97 | 73 | |
| 3 | 66 | 71 | |
| 4 | 77 | 46 | |
| 5 | 71 | 60 | |
| 6 | 51 | 56 | |
| 7 | 72 | 45 | |
| 8 | 70 | 81 | |
| 9 | 44 | 39 | |
| 10 | 57 | 48 | |
| 11 | 53 | 41 | |
| 12 | 22 | 33 | |
| 13 | 78 | 48 | |
| 14 | 49 | 54 | |
| 15 | 60 | 23 | |
| 16 | 42 | 10 | |
| 17 | 54 | 62 | |
| 18 | 56 | 62 | |
| 19 | 41 | 33 | |
| 20 | 56 | 22 | |
| 21 | 30 | 93 | |
| 22 | 59 | 7 | |
| 23 | 90 | 67 | |

-continued

| Example | Abl % @ 10 µM | KDR % @ 10 µM | Flt3% @ 10 µM |
|---|---|---|---|
| 24 | 80 | 70 | |
| 25 | 44 | 73 | |
| 26 | 55 | 56 | |
| 27 | 54 | 51 | |
| 28 | 73 | 61 | |
| 29 | 78 | | |
| 30 | 57 | 37 | |
| 31 | 68 | 83 | |
| 32 | 90 | 37 | |
| 33 | 97 | 51 | |
| 34 | 73 | 89 | |
| 35 | 27 | 47 | |
| 36 | 57 | 77 | |
| 37 | 28 | 82 | |
| 38 | 74 | 91 | |
| 39 | 64 | 74 | |
| 40 | 65 | 78 | |
| 41 | 13 | 52 | |
| 42 | 32 | 56 | |
| 43 | 37 | 63 | |
| 44 | 75 | 97 | |
| 45 | 34 | 61 | |
| 46 | 1 | 43 | |
| 47 | 39 | 74 | |
| 48 | 90 | 50 | |
| 49 | 72 | 37 | |
| 50 | 87 | 83 | |
| 51 | 92 | 52 | |
| 52 | 78 | 37 | |
| 53 | 88 | 79 | |
| 54 | 69 | 74 | |
| 55 | 43 | 54 | |
| 56 | 40 | 44 | |
| 57 | 8 | 42 | |
| 58 | 40 | 26 | |
| 59 | 75 | 83 | |
| 60 | 79 | 36 | |
| 61 | 95 | 65 | |
| 62 | 59 | 44 | |
| 63 | 74 | 82 | |
| 64 | 56 | 59 | |
| 65 | 96 | 60 | |
| 66 | 67 | 23 | |
| 67 | 98 | 88 | 41 |
| 68 | 99 | 96 | |

The invention claimed is:

1. A compound of formula

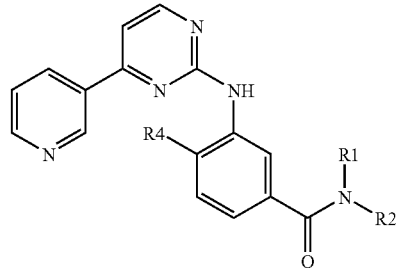

(I)

wherein

R$_1$ and R$_2$ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;

$R_4$ represents hydrogen, lower alkyl, or halogen;

or a N-oxide or pharmaceutically acceptable salts thereof.

2. A compound of formula I according to claim 1 wherein $R_1$ and $R_2$ together represent alkylene with four or five carbon atoms, optionally mono- or disubstituted by lower alkyl, cycloalkyl, heterocyclyl, phenyl, hydroxy, lower alkoxy, amino, mono- or disubstituted amino, pyridyl, pyrazinyl or pyrimidinyl; benzalkylene with four or five carbon atoms in the alkylene group; oxaalkylene with one oxygen and four carbon atoms; or azaalkylene with one nitrogen and four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, phenyl, substituted phenyl, pyridinyl, pyrimidinyl, or pyrazinyl;

$R_4$ represents hydrogen, lower alkyl, or halogen;

or a N-oxide or pharmaceutically acceptable salts thereof.

3. A compound of formula I according to claim 1 wherein $R_1$ and $R_2$ together represent alkylene with four or five carbon atoms, optionally mono- or disubstituted by lower alkyl, cycloalkyl, phenyl, hydroxy, lower alkoxy, amino, benzoylamino, piperidino, pyridyl, pyrazinyl or pyrimidinyl; benzalkylene with four or five carbon atoms in the alkylene group; oxaalkylene with one oxygen and four carbon atoms; or azaalkylene with one nitrogen and four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, carbamoyl-lower alkyl N-mono- or N,N-disubstituted by lower alkyl, phenyl, lower alkylene or oxa-lower alkylene, cycloalkyl, lower alkoxycarbonyl, phenyl, methoxyphenyl, trifluoromethylphenyl, trifluoromethoxyphenyl, pyridinyl, pyrimidinyl, or pyrazinyl;

$R_4$ represents hydrogen or lower alkyl;

or a N-oxide or pharmaceutically acceptable salts thereof.

4. A compound of formula I according to claim 1 wherein $R_1$ and $R_2$ together represent alkylene with four or five carbon atoms, optionally mono- or disubstituted by phenyl, hydroxy, amino, benzoylamino, or piperidino; benzalkylene with four or five carbon atoms in the alkylene group; oxaalkylene with one oxygen and four carbon atoms; or azaalkylene with one nitrogen and four carbon atoms wherein nitrogen is unsubstituted or substituted by lower alkyl, phenyl-lower alkyl, lower alkoxycarbonyl-lower alkyl, carbamoyl-lower alkyl, pyrrolidinocarbonyl-lower alkyl, morpholinocarbonyl-lower alkyl, cyclopentyl, lower alkoxycarbonyl, phenyl, methoxyphenyl, trifluoromethylphenyl, pyridinyl; pyrimidinyl, or pyrazinyl;

$R_4$ represents hydrogen or methyl;

or a N-oxide or pharmaceutically acceptable salts thereof.

5. A process for the synthesis of a compound of the formula

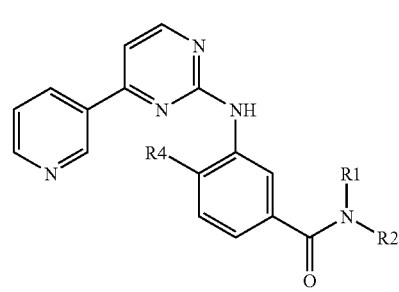

(I)

or an N-oxide or a salt thereof, wherein the symbols $R_1$ $R_2$ and $R_4$ are as defined in claim 1, characterized in that a compound of formula II

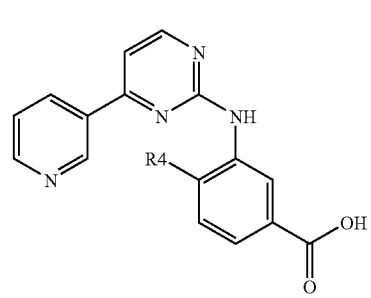

(II)

wherein $R_4$ is as defined for a compound of formula I, wherein the carboxy group —COOH is in activated form, is reacted with an amine of the formula III $R_1$—NH—$R_2$     (III)

wherein $R_1$ and $R_2$ are as defined for a compound of the formula I, optionally in the presence of a dehydrating agent and an inert base and/or a suitable catalyst, and optionally in the presence of an inert solvent;

where the above starting compounds II and III may also be present with functional groups in protected form if necessary and/or in the form of salts, provided a salt-forming group is present and the reaction in salt form is possible;

any protecting groups in a protected derivative of a compound of the formula I are removed;

and, if so desired, an obtainable compound of formula I is converted into another compound of formula I or a N-oxide thereof, a free compound of formula I is converted into a salt, an obtainable salt of a compound of formula I is converted into the free compound or another salt, and/or a mixture of isomeric compounds of formula I is separated into the individual isomers.

6. A pharmaceutical composition comprising as an active ingredient a compound of formula I according to claim 1 or a N-oxide or a pharmaceutically acceptable salt thereof together with a pharmaceutically acceptable carrier.

7. A method for the treatment of leukemia, which comprises administering a compound of formula I according to claim 1 or a N-oxide or a pharmaceutically acceptable salt thereof.

* * * * *